US008877476B2

(12) United States Patent
Newcomer et al.

(10) Patent No.: US 8,877,476 B2
(45) Date of Patent: Nov. 4, 2014

(54) SOLUBLE AND STABLE HUMAN 5-LIPOXYGENASE

(75) Inventors: Marcia E. Newcomer, Baton Rouge, LA (US); Sue G. Bartlett, Baton Rouge, LA (US); Nathaniel C. Gilbert, Nashville, TN (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 142 days.

(21) Appl. No.: 13/700,507

(22) PCT Filed: May 31, 2011

(86) PCT No.: PCT/US2011/038492
§ 371 (c)(1),
(2), (4) Date: Feb. 27, 2013

(87) PCT Pub. No.: WO2011/153121
PCT Pub. Date: Dec. 8, 2011

(65) Prior Publication Data
US 2013/0210052 A1    Aug. 15, 2013

Related U.S. Application Data

(60) Provisional application No. 61/350,197, filed on Jun. 1, 2010.

(51) Int. Cl.
*C12N 9/02* (2006.01)
*C07H 21/04* (2006.01)
*C12Q 1/26* (2006.01)

(52) U.S. Cl.
CPC ....... *C12N 9/0069* (2013.01); *C12Y 113/11034* (2013.01); *C12Q 1/26* (2013.01); *G01N 2500/00* (2013.01)
USPC .......................... 435/189; 536/23.2; 536/23.5

(58) Field of Classification Search
None
See application file for complete search history.

(56) References Cited

PUBLICATIONS

Ago, H. et al., "Crystal Structure of a Human Membrane Protein Involved in Cysteinyl Leukotriene Biosynthesis," Nature, vol. 448, pp. 609-613 (2007).
Aharony, David et al., "Kinetic Mechanism of Guinea Pig Neutrophil 5-Lipoxygenase," J Biol Chem, vol. 261, No. 25, pp. 11512-11519 (1986).
Brash, A.R., J Biol Chem, "Lipoxygenases: Occurrence, Functions, Catalysis, and Acquisition of Substrate," vol. 274, No. 34, pp. 23679-23682 (1999).
Canadillas, J.M. et al., "Solution Structure of p53 Core Domain: Structural Basis for Its Instability," Proc Natl Acad Sci U S A, vol. 103, No. 107, pp. 2109-2114 (2006).
Chen, X-S et al., "The N-terminal "β-Barrel" Domain of 5-Lipoxygenase is Essential for Nuclear Membrane Translocation," J Biol Chem, vol. 276, No. 1, pp. 811-818 (2001).
Chen, X-S et al., "Determinants of 5-Lipoxygenase Nuclear Localization Using Green Fluorescent Protein/5-Lipoxygenase Fusion Proteins," J Biol Chem, vol. 273, No. 47, pp. 31237-31244 (1998).
Choi, J. et al., "Conformational Flexibility in Mammalian 15S-Lipoxygenase: Reinterpretation of the Crystallographic Data," Proteins, vol. 70, pp. 1023-1032 (2008).
Coffa, G. et al., "A Single Active Site Residue Directs Oxygenation Stereospecificity in Lipoxygenases: Stereocontrol is Linked to the Position of Oxygenation," Proc Natl Acad Sci U S A, vol. 101, No. 44, pp. 15579-15584 (2004).
Collaborative Computational Project No. 4, Acta Crystallogr, vol. D50, pp. 760-763 (1994).
Dixon, R.A. et al., "Requirement of a 5-Lipoxygenase_activating Protein for Leukotriene Synthesis," Nature, vol. 343, pp. 282-284 (1990).
Dundas, J. et al., "CASTp: Computed Atlas of Surface Topography of Proteins with Structural and Topographical Mapping of Functionally Annotated Residues," vol. 34, pp. W116-W118 (2006).
Emsley, P. et al., "Coot: Model-building Tools for Molecular Graphics," Acta Crystallogr Sec. D Biol Crystallogr, vol. D60, pp. 2126-2132 (2004).
Ericsson, U.B. et al., "Thermofluor-based High-throughput Stability Optimization of Proteins for Structural Studies," Anal Biochem, vol. 357, pp. 289-298 (2006).
Evans, J.F. et al., "What's all the FLAP about?: 5-lipoxygenase-activating protein inhibitors for inflammatory diseases," Trends Pharmacol Sci, vol. 29, No. 2, pp. 72-78 (2008).
Ferguson, A.D. et al., "Crystal Structure of Inhibitor-Bound Human 5-Lipoxygenase-Activating Protein," Science, vol. 317, pp. 510-512 (2007).
Gilbert, N.C. et al., "The Crystal Structure of Human 5-Lipoxygenase", an abstract and poster for the Keystone Conference, Bioactive Lipids: Biochemistry and Diseases, in Kyoto, Japan, Jun. 6, 2010.
Gilbert, N.C. et al., "The Structure of Human 5-Lipoxygenase," Science, vol. 331, pp. 217-219 (2011).
Gillmor, S.A. et al., "The Structure of Mammalian 15-Lipoxygenase Reveals Similarity to the Lipases and the Determinants of Substrate Specificity," Nat Struct Biol, vol. 4, No. 12, pp. 1003-1009 (1997).
Hammarberg, T. et al., "Calcium Binding to 5-Lipoxygenase," Advances in Experimental Medicine and Biology, vol. 507, pp. 117-121 (2002).

(Continued)

*Primary Examiner* — Suzanne M Noakes
*Assistant Examiner* — Jae W Lee
(74) *Attorney, Agent, or Firm* — Bonnie J. Davis; John H. Runnels

(57) ABSTRACT

A soluble and stable form of 5-lipoxygenase (5-LOX) has been made, 5-Lox is the enzyme which initiates leukotriene biosynthesis by catalyzing the two-step transformation of arachidome acid to leukotriene A4 (LTA4). The soluble and stable 5-LOX is suitable for a number of applications, including, but not limited to, high throughput screening of 5-LOX inhibitors, structural analysis of the enzyme's active site, designing inhibitors based on the three-dimensional structure of the enzyme's active site, and synthesis of LTA4. Using Stable-5-LOX, the crystal structure for 5-LOX has been resolved and the amino acids defining the active site determined.

15 Claims, 14 Drawing Sheets

(56) References Cited

PUBLICATIONS

Hughes, M.A. et al., "Investigation of the Mechanism of Biosynthesis of 8-Hydroxyeicosatetraenoic Acid in Mouse Skin," Biochim Biophys Acta, vol. 1081, No. 3, pp. 347-354 (1991).

Knapp, M.J. et al., "Steric Control of Oxygenation Regiochemistry in Soybean Lipoxygenase-1," J Am Chem Soc, vol. 123, pp. 2931-2932 (2001).

Knapp, M.J. et al., "Kinetic Studies of Oxygen Reactivity in Soybean Lipoxygenase-1," Biochemistry, vol. 42, pp. 11466-11475 (2003).

Kuhn, H. et al., "Amino Acid Differences in the Deduced 5-Lipoxygenase Sequence of CAST Atherosclerosis-Resistance Mice Confer Impaired Activity When Introduced Into the Human Ortholog," Arterioscler Thromb Vasc Biol, vol. 23, 1072-1076 (2003).

Kuhn, H. et al., "The Diversity of the Lipoxygenase Family: Many Sequence Data but Little Information on Biological Significance," FEBS Lett, vol. 449, No. 1, pp. 7-11 (1999).

Kulkarni, S. et al., "Molecular Basis of the Specific Subcellular Localization of the C2-like Domain of 5-Lipoxygenase," J Biol Chem, vol. 277, No. 15, pp. 13167-13174 (2002).

Martinez Molina, D. et al., "Structural Basis for Synthesis of Inflammatory Mediators by Human Leukotriene $C_4$ Synthase," Nature, vol. 448, pp. 613-617 (2007).

Minor, W. et al., "Crystal Structure of Soybean Lipoxygenase L-1 at 1.4 Å Resolution," Biochemistry, vol. 35, pp. 10687-10701 (1996).

Murphy, R.C. et al., "Biosynthesis and Metabolism of Leukotrienes," Biochem J, vol. 405, pp. 379-395 (2007).

Neau, D.B. et al., "Improving Protein Crystal Quality by Selective Removal of a $Ca^{2+}$-dependent Membrane-Insertion Loop," Acta Crystallographica, Section F63, pp. 972-975 (2007).

Neau, David B. et al., "The 1.85 Å Structure of an *8R*-Lipoxygenase Suggests a General Model for Lipoxygenase Product Specificity," Biochemistry, vol. 48, pp. 7906-7915 (2009).

Oldham, M.L. et al., "Insights from the X-ray Crystal Structure of Coral 8R-Lipoxygenase," J Biol Chem, vol. 280, No. 47, pp. 39545-39552 (2005).

Percival, M.D. et al., "Investigation of the Mechanism of Non-turn-over-dependent Inactivation of Purified Human 5-lipoxygenase," Eur J Biochem, vol. 210, pp. 109-117 (1992).

Radmark, Olol et al., J. Lipid Res, April Suppl, pp. s40-S45 (2009).

Schneider, C. et al., "Control of Oxygenation in Lipoxygenase and Cyclooxygenase Catalysis," Chem & Biol, vol. 14, pp. 473-488 (2007).

Shimizu, T. et al., "Enzyme with Dual Lipoxygenase Activities Catalyzes Leukotriene $A_4$ Synthesis from Arachidonic Acid," Proc.Natl Acad Sci USA, vol. 81, pp. 689-693 (1984).

Studier, F.W., Protein Production by Auto-Induction in High-Density Shaking Cultures, Protein Expr Purif, vol. 41, pp. 207-234 (2005).

Walther, M. et al., "Alterations of Lipoxygenase Specificity by Targeted Substrate Modification and Site-Directed Mutagenesis," Chem & Biol, vol. 8, pp. 779-790 (2001).

Zhang, Y-Y et al., "Stabilization of Purified Human 5-Lipoxygenase with Glutathione Peroxidase and Superoxide Dismutase," Anal Biochem, vol. 220, pp. 28-35 (1994).

Zwart, P.H. et al., "Automated Structure Solution with the PHENIX Suite," Methods Mol Biol, vol. 426, Chapter 28, pp. 419-435 (2008).

SEQ ID NO: 1 — Native protein (human 5-LOX)

| | | | | | |
|---|---|---|---|---|---|
| PSYTVTVATG | SQWFAGTDDY | IYLSLVGSAG | CSEKHLLDKP | FYNDFERGAV | DSYDVTVDEE 60 |
| LGEIQLVRIE | KRKYWLNDDW | YLKYITLKTP | HGDYIEFPCY | RWITGDVEVV | LRDGRAKLAR 120 |
| DDQIHILKQH | RRKELETRQK | QYRWMEWNPG | FPLSIDAKCH | KDLPRDIQFD | SEKGVDFVLN 180 |
| YSKAMENLFI | NRFMHMFQSS | WNDFADFEKI | FVKISNTISE | RVMNHWQEDL | MFGYQFLNGC 240 |
| NPVLIRRCTE | LPEKLPVTTE | MVECSLERQL | SLEQEVQQGN | IFIVDFELLD | GIDANKTDPC 300 |
| TLQFLAAPIC | LLYKNLANKI | VPIAIQLNQI | PGDENPIFLP | SDAKYDWLLA | KIWVRSSDFH 360 |
| VHQTITHLLR | THLVSEVFGI | AMYRQLPAVH | PIFKLLVAHV | RFTIAINTKA | REQLICECGL 420 |
| FDKANATGGG | GHVQMVQRAM | KDLTYASLCF | PEAIKARGME | SKEDIPYYFY | RDDGLLVWEA 480 |
| IRTFTAEVVD | IYYEGDQVVE | EDPELQDFVN | DVYVYGMRGR | KSSGFPKSVK | SREQLSEYLT 540 |
| VVIFTASAQH | AAVNFGQYDW | CSWIPNAPPT | MRAPPPTAKG | VVTIEQIVDT | LPDRGRSCWH 600 |
| LGAVWALSQF | QENELFLGMY | PEEHFIEKPV | KEAMARFRKN | LEAIVSVIAE | RNKKKQLPYY 660 |
| YLSPDRIPNS | VAI | | | | 673 |

Fig. 1

SEQ ID NO: 2 — Sol-5-LOX

```
MGSSHHHHHH SSGLVPRGSH MPSYTVTVAT GSQEHAGTDD YIYLSLVGSA GCSEKHLLDK    60
GSFERGAVDS YDVTVDEELG EIQLVRIEKR KYGSNDDWYL KYITLKTPHG DYIEFPCYRW   120
ITGDVEVVLR DGRAKLARDD QIHILKQHRR KELETRQKQY RWMEWNPGFP LSIDAKCHKD   180
LPRDIQFDSE KGVDFVLNYS KAMENLFINR FMHMFQSSWN DFADFEKIFV KISNTISERV   240
MNHWQEDLMF GYQFLNGANP VLIRRCTELP EKLPVTTEMV ECSLERQLSL EQEVQQGNIF   300
IVDFELLDGI DANKTDPCTL QFLAAPICLL YKNLANKIVP IAIQLNQIPG DENPIFLPSD   360
AKYDWLLAKI WVRSSDFHVH QTITHLLRTH LVSEVFGIAM YRQLPAVHPI FKLLVAHVRF   420
TIAINTKARE QLICECGLFD KANATGGGGH VQMVQRAMKD LTYASLCFPE AIKARGMESK   480
EDIPYFYRD DGLLVWEAIR TFTAEVVDIY YEGDQVVEED PELQDFVNDV YVYGMRGRKS   540
SGFPKSVKSR EQLSEYLTVV IFTASAQHAA VNFGQYDWAS WIPNAPPTMR APPPTAKGVV   600
TIEQIVDTLP DRGRSCWHLG AVWALSQFQE NELFLGMYPE EHFIEKPVKE AMARFRKNLE   660
AIVSVIAERN KKKQLPYYYL SPDRIPNSVA I                                  691
```

Fig. 2

SEQ ID NO: 3 — Stable-5-LOX

| | | | | | |
|---|---|---|---|---|---|
| MGSSHHHHHH | SSGLVPRGSH | MPSYTVTVAT | GSQEHAGTDD | YIYLSLVGSA | GCSEKHLLDK | 60
| GSFERGAVDS | YDVTVDEELG | EIQLVRIEKR | KYGSNDDWYL | KYITLKTPHG | DYIEFPCYRW | 120
| ITGDVEVVLR | DGRAKLARDD | QIHILKQHRR | KELETRQKQY | RWMEWNPGFP | LSIDAKCHKD | 180
| LPRDIQFDSE | KGVDFVLNYS | KAMENLFINR | FMHMFQSSWN | DFADFEKIFV | KISNTISERV | 240
| MNHWQEDLMF | GYQFLNGANP | VLIRRCTELP | EKLPVTTEMV | ECSLERQLSL | EQEVQQGNIF | 300
| IVDFELLDGI | DANKTDPCTL | QFLAAPICLL | YKNLANKIVP | IAIQLNQIPG | DENPIFLPSD | 360
| AKYDWLLAKI | WVRSSDFHVH | QTITHLLRTH | LVSEVFGIAM | YRQLPAVHPI | FKLLVAHVRF | 420
| TIAINTKARE | QLICECGLFD | KANATGGGGH | VQMVQRAMKD | LTYASLCFPE | AIKARGMESK | 480
| EDIPYYFYRD | DGLLVWEAIR | TFTAEVVDIY | YEGDQVVEED | PELQDFVNDV | YVYGMRGRKS | 540
| SGFPKSVKSR | EQLSEYLTVV | IFTASAQHAA | VNFGQYDWAS | WIPNAPPTMR | APPPTAKGVV | 600
| TIEQIVDTLP | DRGRSCWHLG | AVWALSQFQE | NELFLGMYPE | EHFIEKPVKE | AMARFRKNLE | 660
| AIVSVIAERN | ENLQLPYYYL | SPDRIPNSVA | I | | | 691

Fig. 3

SEQ ID NO: 4 — S663D-Stable-5-LOX

```
MGSSHHHHHH SSGLVPRGSH MPSYTVTVAT GSQEHAGTDD YIYLSLVGSA GCSEKHLLDK    60
GSFERGAVDS YDVTVDEELG EIQLVRIEKR KYGSNDDWYL KYITLKTPHG DYIEFPCYRW   120
ITGDVEVVLR DGRAKLARDD QIHILKQHRR KELETRQKQY RWMEWNPGFP LSIDAKCHKD   180
LPRDIQFDSE KGVDFVLNYS KAMENLFINR ANP FMHMFQSSWN DFADFEKIFV KISNTISERV   240
MNHWQEDLMF GYQFLNGANP VLIRRCTELP EKLPVTTEMV ECSLERQLSL EQEVQQGNIF   300
IVDFELLDGI DANKTDPCTL QFLAAPICLL YKNLANKIVP TAIQLNQIPG DENPIFLPSD   360
AKYDWLLAKI WVRSSDFHVH QTITHLLRTH LVSEVFGIAM YRQLPAVHPI FKLLVAHVRF   420
TIAINTKARE QLICECGLFD KANATGGGGH VQMVQRAMKD LTYASLCFPE AIKARGMESK   480
EDIPYFYRD DGLLWEAIR TFTAEVVDIY YEGDQVVEED PELQDFVNDV VVYGMRGRKS   540
SGFPKSVKSR EQLSEYLTVV IFTASAQHAA VNFGQYDWAS WIPNAPPTMR APPPTAKGVV   600
TIEQIVDTLP DRGRSCWHLG AVWALSQFQE NELFLGMYPE EHFIEKPVKE AMARFRKNLE   660
AIVSVIAERN ENLQLPYYYL DPDRIPNSVA I                                 691
```

Fig. 4

| Species | Sequence | Length | SEQ ID |
|---|---|---|---|
| H. sapiens | VSVIAERNKKKQLPYYYLSPDRIPNSVAI | 673 | SEQ ID NO: 1 (645-673aa) |
| B. taurus | VSVIAERNKNKKLPYYYLSPDRIPNSVAI | 674 | SEQ ID NO: 6 |
| S. scrofa | VSVIAERNKDKKLPYYYLSPDRIPNSVAI | 675 | SEQ ID NO: 7 |
| M. mulata | VSVIAERNKKKQLPYYYLSPDRIPNSVAI | 674 | SEQ ID NO: 8 |
| M. musculus | VSVIAERNKNKKLPYYYLSPDRIPNSVAI | 674 | SEQ ID NO: 9 |
| M. auratus | VNVIAERNKNKKLPYYYLSPDRIPNSVAI | 673 | SEQ ID NO: 10 |
| O. cuniculus | VSVIAERNKHKKLPYYYLSPDRIPNSVAI | 674 | SEQ ID NO: 11 |
| M. domestica | VSGITERNKNKKLPYYYLSPDRIPNSVAI | 674 | SEQ ID NO: 12 |
| D. rerio | SKTIKNRNEGKKLPYYFSPDRIPNSVAV | 674 | SEQ ID NO: 13 |
| S. salar | SSAIKIRNEGKKLPYYYSPDRIPNSVAV | 674 | SEQ ID NO: 14 |
| H. sapiens-12R | SHDIRQRNKCLPIPYYYLDPVLIENSISI | 701 | SEQ ID NO: 15 |
| H. sapiens-E3 | SRDIQERNQGLALPYTYLDPPLIENSVSI | 711 | SEQ ID NO: 16 |
| H. sapiens-15B | SRGIQERNQGLVLPYTYLDPPLIENSVSI | 676 | SEQ ID NO: 17 |
| H. sapiens-15A | DKEIEIRNAKLDMPYEYLRPSVVENSVAI | 662 | SEQ ID NO: 18 |
| O. cuniculus-15 | DKEIEVRNEKLDIPYEYLRPSIVENSVAI | 663 | SEQ ID NO: 19 |
| H. sapiens-12S | EKEITARNEQLDWPYEYLKPSCIENSVTI | 663 | SEQ ID NO: 20 |
| P. homomalla-8R | SKKIKQRNENLEVPYIYLLPERIPNGTAI | 694 | SEQ ID NO: 21 |

Fig. 5

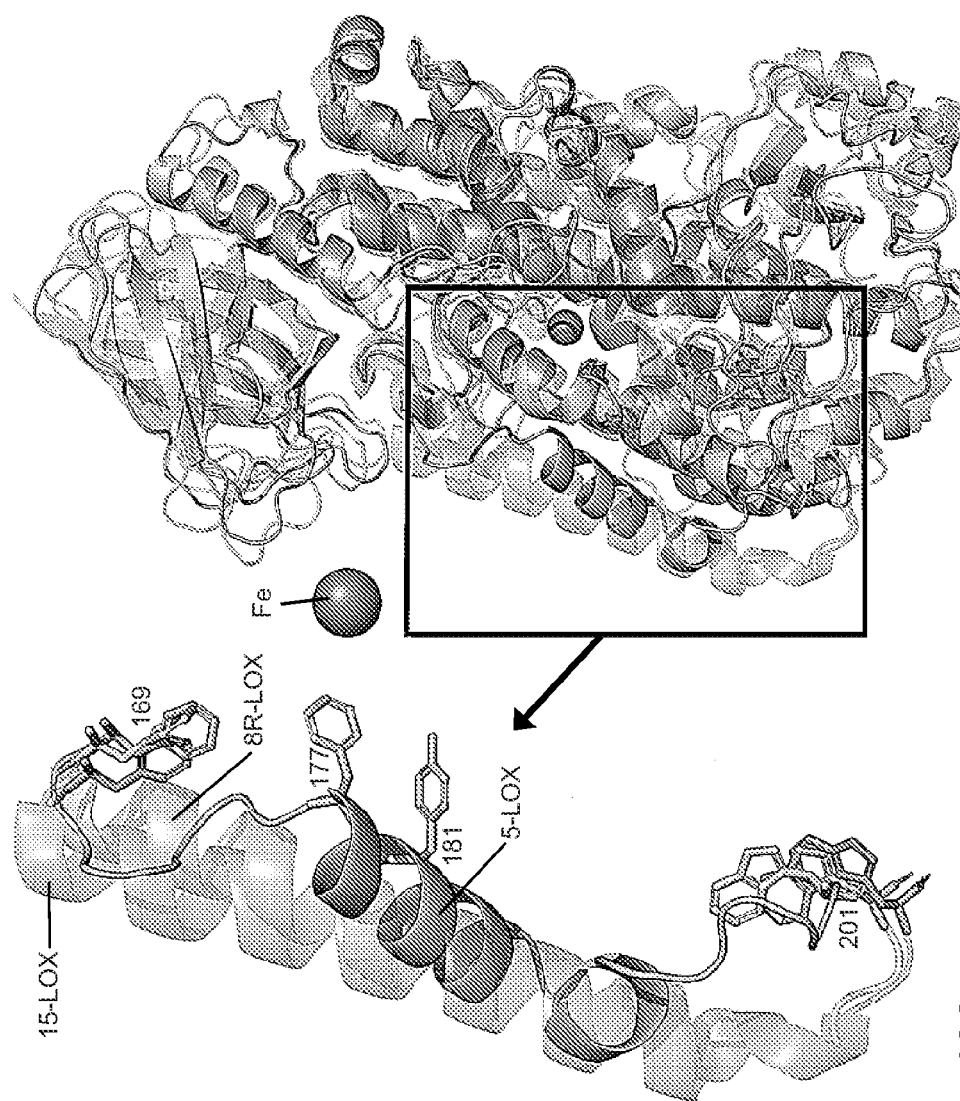

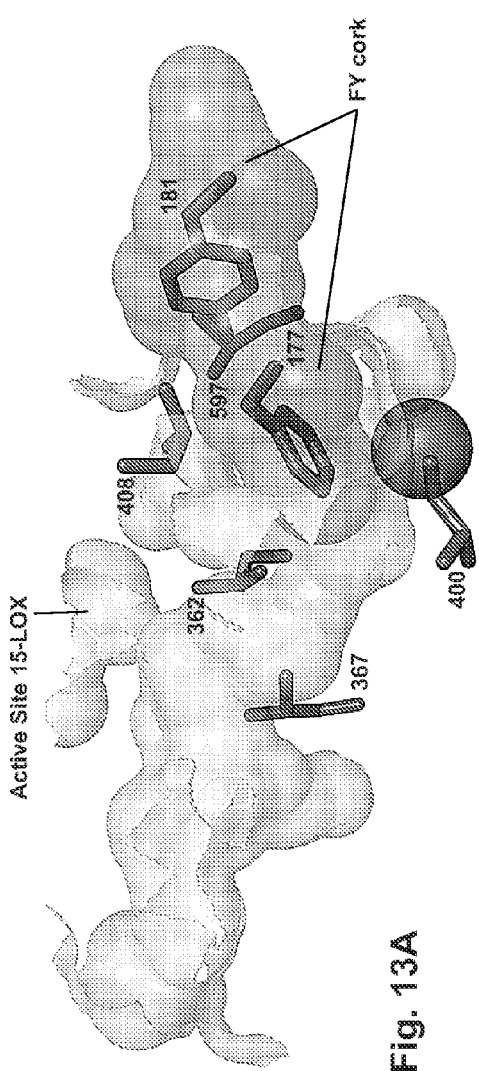
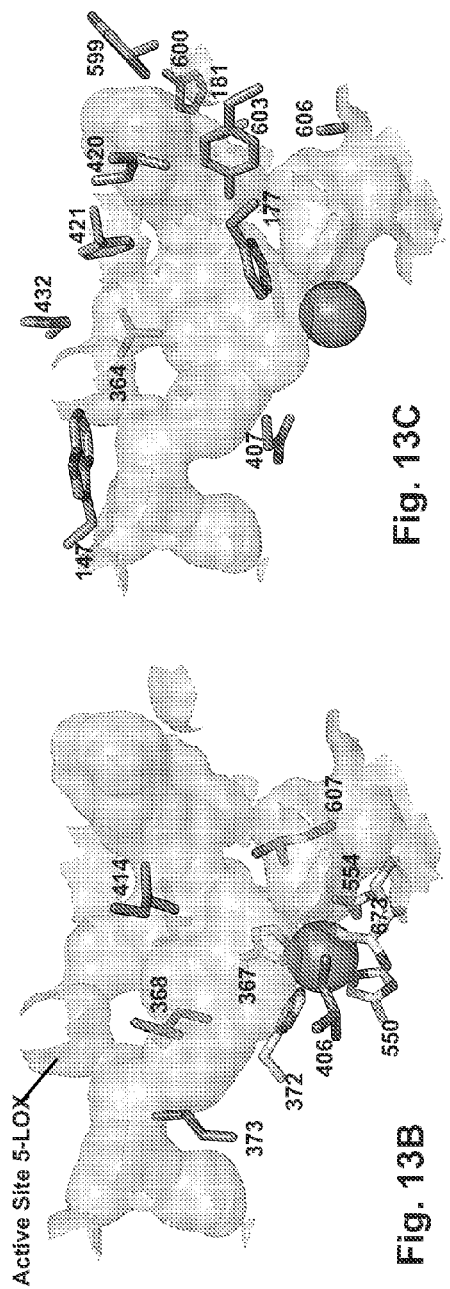
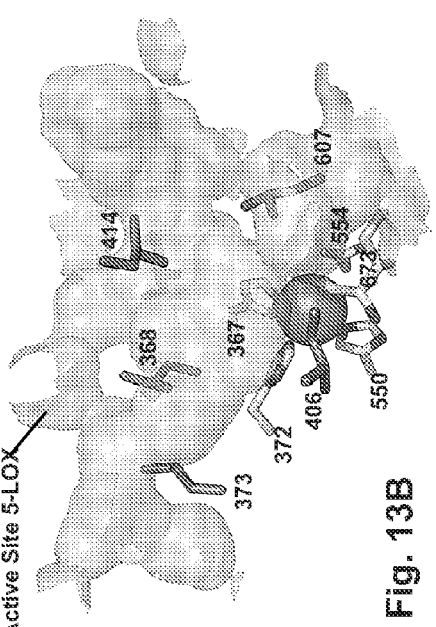
Fig. 13A
Fig. 13B
Fig. 13C

```
                         SEQUENCE LISTING

<160> NUMBER OF SEQ ID NOS: 21

<210> SEQ ID NO 1
<211> LENGTH: 673
<212> TYPE: PRT
<213> ORGANISM: Human 5-LOX

<400> SEQUENCE: 1

Pro Ser Tyr Thr Val Thr Val Ala Thr Gly Ser Gln Trp Phe Ala Gly
1               5                   10                  15

Thr Asp Asp Tyr Ile Tyr Leu Ser Leu Val Gly Ser Ala Gly Cys Ser
            20                  25                  30

Glu Lys His Leu Leu Asp Lys Pro Phe Tyr Asn Asp Phe Glu Arg Gly
        35                  40                  45

Ala Val Asp Ser Tyr Asp Val Thr Val Asp Glu Glu Leu Gly Glu Ile
    50                  55                  60

Gln Leu Val Arg Ile Glu Lys Arg Lys Tyr Trp Leu Asn Asp Asp Trp
65                  70                  75                  80

Tyr Leu Lys Tyr Ile Thr Leu Lys Thr Pro His Gly Asp Tyr Ile Glu
                85                  90                  95

Phe Pro Cys Tyr Arg Trp Ile Thr Gly Asp Val Glu Val Val Leu Arg
            100                 105                 110

Asp Gly Arg Ala Lys Leu Ala Arg Asp Asp Gln Ile His Ile Leu Lys
        115                 120                 125

Gln His Arg Arg Lys Glu Leu Glu Thr Arg Gln Lys Gln Tyr Arg Trp
    130                 135                 140

Met Glu Trp Asn Pro Gly Phe Pro Leu Ser Ile Asp Ala Lys Cys His
145                 150                 155                 160

Lys Asp Leu Pro Arg Asp Ile Gln Phe Asp Ser Glu Lys Gly Val Asp
                165                 170                 175

Phe Val Leu Asn Tyr Ser Lys Ala Met Glu Asn Leu Phe Ile Asn Arg
            180                 185                 190

Phe Met His Met Phe Gln Ser Ser Trp Asn Asp Phe Ala Asp Phe Glu
        195                 200                 205

Lys Ile Phe Val Lys Ile Ser Asn Thr Ile Ser Glu Arg Val Met Asn
    210                 215                 220

His Trp Gln Glu Asp Leu Met Phe Gly Tyr Gln Phe Leu Asn Gly Cys
225                 230                 235                 240

Asn Pro Val Leu Ile Arg Arg Cys Thr Glu Leu Pro Glu Lys Leu Pro
                245                 250                 255

Val Thr Thr Glu Met Val Glu Cys Ser Leu Glu Arg Gln Leu Ser Leu
            260                 265                 270

Glu Gln Glu Val Gln Gln Gly Asn Ile Phe Ile Val Asp Phe Glu Leu
        275                 280                 285

Leu Asp Gly Ile Asp Ala Asn Lys Thr Asp Pro Cys Thr Leu Gln Phe
    290                 295                 300

Leu Ala Ala Pro Ile Cys Leu Leu Tyr Lys Asn Leu Ala Asn Lys Ile
305                 310                 315                 320

Val Pro Ile Ala Ile Gln Leu Asn Gln Ile Pro Gly Asp Glu Asn Pro
                325                 330                 335

Ile Phe Leu Pro Ser Asp Ala Lys Tyr Asp Trp Leu Leu Ala Lys Ile
```

```
            340                 345                 350
Trp Val Arg Ser Ser Asp Phe His Val His Gln Thr Ile Thr His Leu
        355                 360                 365
Leu Arg Thr His Leu Val Ser Glu Val Phe Gly Ile Ala Met Tyr Arg
    370                 375                 380
Gln Leu Pro Ala Val His Pro Ile Phe Lys Leu Val Ala His Val
385                 390                 395                 400
Arg Phe Thr Ile Ala Ile Asn Thr Lys Ala Arg Glu Gln Leu Ile Cys
                405                 410                 415
Glu Cys Gly Leu Phe Asp Lys Ala Asn Ala Thr Gly Gly Gly His
            420                 425                 430
Val Gln Met Val Gln Arg Ala Met Lys Asp Leu Thr Tyr Ala Ser Leu
        435                 440                 445
Cys Phe Pro Glu Ala Ile Lys Ala Arg Gly Met Glu Ser Lys Glu Asp
    450                 455                 460
Ile Pro Tyr Tyr Phe Tyr Arg Asp Asp Gly Leu Leu Val Trp Glu Ala
465                 470                 475                 480
Ile Arg Thr Phe Thr Ala Glu Val Val Asp Ile Tyr Tyr Glu Gly Asp
                485                 490                 495
Gln Val Val Glu Glu Asp Pro Glu Leu Gln Asp Phe Val Asn Asp Val
            500                 505                 510
Tyr Val Tyr Gly Met Arg Gly Arg Lys Ser Ser Gly Phe Pro Lys Ser
        515                 520                 525
Val Lys Ser Arg Glu Gln Leu Ser Glu Tyr Leu Thr Val Ile Phe
    530                 535                 540
Thr Ala Ser Ala Gln His Ala Ala Val Asn Phe Gly Gln Tyr Asp Trp
545                 550                 555                 560
Cys Ser Trp Ile Pro Asn Ala Pro Pro Thr Met Arg Ala Pro Pro Pro
                565                 570                 575
Thr Ala Lys Gly Val Val Thr Ile Glu Gln Ile Val Asp Thr Leu Pro
            580                 585                 590
Asp Arg Gly Arg Ser Cys Trp His Leu Gly Ala Val Trp Ala Leu Ser
        595                 600                 605
Gln Phe Gln Glu Asn Glu Leu Phe Leu Gly Met Tyr Pro Glu Glu His
    610                 615                 620
Phe Ile Glu Lys Pro Val Lys Glu Ala Met Ala Arg Phe Arg Lys Asn
625                 630                 635                 640
Leu Glu Ala Ile Val Ser Val Ile Ala Glu Arg Asn Lys Lys Gln
                645                 650                 655
Leu Pro Tyr Tyr Tyr Leu Ser Pro Asp Arg Ile Pro Asn Ser Val Ala
            660                 665                 670
Ile

<210> SEQ ID NO 2
<211> LENGTH: 691
<212> TYPE: PRT
<213> ORGANISM: Sol-5-LOX

<400> SEQUENCE: 2

Met Gly Ser Ser His His His His His His Ser Ser Gly Leu Val Pro
1               5                   10                  15
Arg Gly Ser His Met Pro Ser Tyr Thr Val Thr Val Ala Thr Gly Ser
                20                  25                  30
Gln Glu His Ala Gly Thr Asp Asp Tyr Ile Tyr Leu Ser Leu Val Gly
```

```
                35                  40                  45
Ser Ala Gly Cys Ser Glu Lys His Leu Leu Asp Lys Gly Ser Phe Glu
 50                  55                  60

Arg Gly Ala Val Asp Ser Tyr Asp Val Thr Val Asp Glu Glu Leu Gly
 65                  70                  75                  80

Glu Ile Gln Leu Val Arg Ile Glu Lys Arg Lys Tyr Gly Ser Asn Asp
                     85                  90                  95

Asp Trp Tyr Leu Lys Tyr Ile Thr Leu Lys Thr Pro His Gly Asp Tyr
                100                 105                 110

Ile Glu Phe Pro Cys Tyr Arg Trp Ile Thr Gly Asp Val Glu Val Val
                115                 120                 125

Leu Arg Asp Gly Arg Ala Lys Leu Ala Arg Asp Asp Gln Ile His Ile
                130                 135                 140

Leu Lys Gln His Arg Arg Lys Glu Leu Glu Thr Arg Gln Lys Gln Tyr
145                 150                 155                 160

Arg Trp Met Glu Trp Asn Pro Gly Phe Pro Leu Ser Ile Asp Ala Lys
                    165                 170                 175

Cys His Lys Asp Leu Pro Arg Asp Ile Gln Phe Asp Ser Glu Lys Gly
                180                 185                 190

Val Asp Phe Val Leu Asn Tyr Ser Lys Ala Met Glu Asn Leu Phe Ile
                195                 200                 205

Asn Arg Phe Met His Met Phe Gln Ser Ser Trp Asn Asp Phe Ala Asp
210                 215                 220

Phe Glu Lys Ile Phe Val Lys Ile Ser Asn Thr Ile Ser Glu Arg Val
225                 230                 235                 240

Met Asn His Trp Gln Glu Asp Leu Met Phe Gly Tyr Gln Phe Leu Asn
                    245                 250                 255

Gly Ala Asn Pro Val Leu Ile Arg Arg Cys Thr Glu Leu Pro Glu Lys
                260                 265                 270

Leu Pro Val Thr Thr Glu Met Val Glu Cys Ser Leu Glu Arg Gln Leu
                275                 280                 285

Ser Leu Glu Gln Glu Val Gln Gln Gly Asn Ile Phe Ile Val Asp Phe
290                 295                 300

Glu Leu Leu Asp Gly Ile Asp Ala Asn Lys Thr Asp Pro Cys Thr Leu
305                 310                 315                 320

Gln Phe Leu Ala Ala Pro Ile Cys Leu Leu Tyr Lys Asn Leu Ala Asn
                325                 330                 335

Lys Ile Val Pro Ile Ala Ile Gln Leu Asn Gln Ile Pro Gly Asp Glu
                340                 345                 350

Asn Pro Ile Phe Leu Pro Ser Asp Ala Lys Tyr Asp Trp Leu Leu Ala
                355                 360                 365

Lys Ile Trp Val Arg Ser Ser Asp Phe His Val His Gln Thr Ile Thr
                370                 375                 380

His Leu Leu Arg Thr His Leu Val Ser Glu Val Phe Gly Ile Ala Met
385                 390                 395                 400

Tyr Arg Gln Leu Pro Ala Val His Pro Ile Phe Lys Leu Leu Val Ala
                405                 410                 415

His Val Arg Phe Thr Ile Ala Ile Asn Thr Lys Ala Arg Glu Gln Leu
                420                 425                 430

Ile Cys Glu Cys Gly Leu Phe Asp Lys Ala Asn Ala Thr Gly Gly Gly
                435                 440                 445

Gly His Val Gln Met Val Gln Arg Ala Met Lys Asp Leu Thr Tyr Ala
                450                 455                 460
```

-continued

Ser Leu Cys Phe Pro Glu Ala Ile Lys Ala Arg Gly Met Glu Ser Lys
465                 470                 475                 480

Glu Asp Ile Pro Tyr Tyr Phe Tyr Arg Asp Asp Gly Leu Leu Val Trp
            485                 490                 495

Glu Ala Ile Arg Thr Phe Thr Ala Glu Val Val Asp Ile Tyr Tyr Glu
        500                 505                 510

Gly Asp Gln Val Val Glu Glu Asp Pro Glu Leu Gln Asp Phe Val Asn
    515                 520                 525

Asp Val Tyr Val Tyr Gly Met Arg Gly Arg Lys Ser Ser Gly Phe Pro
530                 535                 540

Lys Ser Val Lys Ser Arg Glu Gln Leu Ser Glu Tyr Leu Thr Val Val
545                 550                 555                 560

Ile Phe Thr Ala Ser Ala Gln His Ala Ala Val Asn Phe Gly Gln Tyr
                565                 570                 575

Asp Trp Ala Ser Trp Ile Pro Asn Ala Pro Pro Thr Met Arg Ala Pro
            580                 585                 590

Pro Pro Thr Ala Lys Gly Val Val Thr Ile Glu Gln Ile Val Asp Thr
        595                 600                 605

Leu Pro Asp Arg Gly Arg Ser Cys Trp His Leu Gly Ala Val Trp Ala
    610                 615                 620

Leu Ser Gln Phe Gln Glu Asn Glu Leu Phe Leu Gly Met Tyr Pro Glu
625                 630                 635                 640

Glu His Phe Ile Glu Lys Pro Val Lys Glu Ala Met Ala Arg Phe Arg
                645                 650                 655

Lys Asn Leu Glu Ala Ile Val Ser Val Ile Ala Glu Arg Asn Lys Lys
            660                 665                 670

Lys Gln Leu Pro Tyr Tyr Tyr Leu Ser Pro Asp Arg Ile Pro Asn Ser
        675                 680                 685

Val Ala Ile
    690

<210> SEQ ID NO 3
<211> LENGTH: 691
<212> TYPE: PRT
<213> ORGANISM: Stable-5-LOX

<400> SEQUENCE: 3

Met Gly Ser Ser His His His His His His Ser Ser Gly Leu Val Pro
1               5                   10                  15

Arg Gly Ser His Met Pro Ser Tyr Thr Val Thr Val Ala Thr Gly Ser
            20                  25                  30

Gln Glu His Ala Gly Thr Asp Asp Tyr Ile Tyr Leu Ser Leu Val Gly
        35                  40                  45

Ser Ala Gly Cys Ser Glu Lys His Leu Leu Asp Lys Gly Ser Phe Glu
    50                  55                  60

Arg Gly Ala Val Asp Ser Tyr Asp Val Thr Val Asp Glu Glu Leu Gly
65                  70                  75                  80

Glu Ile Gln Leu Val Arg Ile Glu Lys Arg Lys Tyr Gly Ser Asn Asp
                85                  90                  95

Asp Trp Tyr Leu Lys Tyr Ile Thr Leu Lys Thr Pro His Gly Asp Tyr
            100                 105                 110

Ile Glu Phe Pro Cys Tyr Arg Trp Ile Thr Gly Asp Val Glu Val Val
        115                 120                 125

Leu Arg Asp Gly Arg Ala Lys Leu Ala Arg Asp Asp Gln Ile His Ile

```
            130                 135                 140
Leu Lys Gln His Arg Arg Lys Glu Leu Glu Thr Arg Gln Lys Gln Tyr
145                 150                 155                 160
Arg Trp Met Glu Trp Asn Pro Gly Phe Pro Leu Ser Ile Asp Ala Lys
                165                 170                 175
Cys His Lys Asp Leu Pro Arg Asp Ile Gln Phe Asp Ser Glu Lys Gly
            180                 185                 190
Val Asp Phe Val Leu Asn Tyr Ser Lys Ala Met Glu Asn Leu Phe Ile
        195                 200                 205
Asn Arg Phe Met His Met Phe Gln Ser Ser Trp Asn Asp Phe Ala Asp
210                 215                 220
Phe Glu Lys Ile Phe Val Lys Ile Ser Asn Thr Ile Ser Glu Arg Val
225                 230                 235                 240
Met Asn His Trp Gln Glu Asp Leu Met Phe Gly Tyr Gln Phe Leu Asn
                245                 250                 255
Gly Ala Asn Pro Val Leu Ile Arg Arg Cys Thr Glu Leu Pro Glu Lys
            260                 265                 270
Leu Pro Val Thr Thr Glu Met Val Glu Cys Ser Leu Glu Arg Gln Leu
        275                 280                 285
Ser Leu Glu Gln Glu Val Gln Gln Gly Asn Ile Phe Ile Val Asp Phe
290                 295                 300
Glu Leu Leu Asp Gly Ile Asp Ala Asn Lys Thr Asp Pro Cys Thr Leu
305                 310                 315                 320
Gln Phe Leu Ala Ala Pro Ile Cys Leu Leu Tyr Lys Asn Leu Ala Asn
                325                 330                 335
Lys Ile Val Pro Ile Ala Ile Gln Leu Asn Gln Ile Pro Gly Asp Glu
            340                 345                 350
Asn Pro Ile Phe Leu Pro Ser Asp Ala Lys Tyr Asp Trp Leu Leu Ala
        355                 360                 365
Lys Ile Trp Val Arg Ser Ser Asp Phe His Val His Gln Thr Ile Thr
370                 375                 380
His Leu Leu Arg Thr His Leu Val Ser Glu Val Phe Gly Ile Ala Met
385                 390                 395                 400
Tyr Arg Gln Leu Pro Ala Val His Pro Ile Phe Lys Leu Leu Val Ala
                405                 410                 415
His Val Arg Phe Thr Ile Ala Ile Asn Thr Lys Ala Arg Glu Gln Leu
            420                 425                 430
Ile Cys Glu Cys Gly Leu Phe Asp Lys Ala Asn Ala Thr Gly Gly Gly
        435                 440                 445
Gly His Val Gln Met Val Gln Arg Ala Met Lys Asp Leu Thr Tyr Ala
450                 455                 460
Ser Leu Cys Phe Pro Glu Ala Ile Lys Ala Arg Gly Met Glu Ser Lys
465                 470                 475                 480
Glu Asp Ile Pro Tyr Tyr Phe Tyr Arg Asp Asp Gly Leu Leu Val Trp
                485                 490                 495
Glu Ala Ile Arg Thr Phe Thr Ala Glu Val Val Asp Ile Tyr Tyr Glu
            500                 505                 510
Gly Asp Gln Val Val Glu Glu Asp Pro Glu Leu Gln Asp Phe Val Asn
        515                 520                 525
Asp Val Tyr Val Tyr Gly Met Arg Gly Arg Lys Ser Ser Gly Phe Pro
530                 535                 540
Lys Ser Val Lys Ser Arg Glu Gln Leu Ser Glu Tyr Leu Thr Val Val
545                 550                 555                 560
```

```
Ile Phe Thr Ala Ser Ala Gln His Ala Val Asn Phe Gly Gln Tyr
                565                 570                 575

Asp Trp Ala Ser Trp Ile Pro Asn Ala Pro Pro Thr Met Arg Ala Pro
            580                 585                 590

Pro Pro Thr Ala Lys Gly Val Val Thr Ile Glu Gln Ile Val Asp Thr
        595                 600                 605

Leu Pro Asp Arg Gly Arg Ser Cys Trp His Leu Gly Ala Val Trp Ala
    610                 615                 620

Leu Ser Gln Phe Gln Glu Asn Glu Leu Phe Leu Gly Met Tyr Pro Glu
625                 630                 635                 640

Glu His Phe Ile Glu Lys Pro Val Lys Glu Ala Met Ala Arg Phe Arg
                645                 650                 655

Lys Asn Leu Glu Ala Ile Val Ser Val Ile Ala Glu Arg Asn Glu Asn
            660                 665                 670

Leu Gln Leu Pro Tyr Tyr Tyr Leu Ser Pro Asp Arg Ile Pro Asn Ser
        675                 680                 685

Val Ala Ile
    690
```

<210> SEQ ID NO 4
<211> LENGTH: 691
<212> TYPE: PRT
<213> ORGANISM: S663D-Stable-5-LOX
<400> SEQUENCE: 4

```
Met Gly Ser Ser His His His His His Ser Ser Gly Leu Val Pro
1               5                   10                  15

Arg Gly Ser His Met Pro Ser Tyr Thr Val Thr Val Ala Thr Gly Ser
                20                  25                  30

Gln Glu His Ala Gly Thr Asp Asp Tyr Ile Tyr Leu Ser Leu Val Gly
            35                  40                  45

Ser Ala Gly Cys Ser Glu Lys His Leu Leu Asp Lys Gly Ser Phe Glu
    50                  55                  60

Arg Gly Ala Val Asp Ser Tyr Asp Val Thr Val Asp Glu Glu Leu Gly
65                  70                  75                  80

Glu Ile Gln Leu Val Arg Ile Glu Lys Arg Lys Tyr Gly Ser Asn Asp
                85                  90                  95

Asp Trp Tyr Leu Lys Tyr Ile Thr Leu Lys Thr Pro His Gly Asp Tyr
            100                 105                 110

Ile Glu Phe Pro Cys Tyr Arg Trp Ile Thr Gly Asp Val Glu Val Val
        115                 120                 125

Leu Arg Asp Gly Arg Ala Lys Leu Ala Arg Asp Asp Gln Ile His Ile
    130                 135                 140

Leu Lys Gln His Arg Arg Lys Glu Leu Glu Thr Arg Gln Lys Gln Tyr
145                 150                 155                 160

Arg Trp Met Glu Trp Asn Pro Gly Phe Pro Leu Ser Ile Asp Ala Lys
                165                 170                 175

Cys His Lys Asp Leu Pro Arg Asp Ile Gln Phe Asp Ser Glu Lys Gly
            180                 185                 190

Val Asp Phe Val Leu Asn Tyr Ser Lys Ala Met Glu Asn Leu Phe Ile
        195                 200                 205

Asn Arg Phe Met His Met Phe Gln Ser Ser Trp Asn Asp Phe Ala Asp
    210                 215                 220

Phe Glu Lys Ile Phe Val Lys Ile Ser Asn Thr Ile Ser Glu Arg Val
```

-continued

```
               225                 230                 235                 240
       Met Asn His Trp Gln Glu Asp Leu Met Phe Gly Tyr Gln Phe Leu Asn
                       245                 250                 255

Gly Ala Asn Pro Val Leu Ile Arg Arg Cys Thr Glu Leu Pro Glu Lys
                       260                 265                 270

Leu Pro Val Thr Thr Glu Met Val Glu Cys Ser Leu Glu Arg Gln Leu
                       275                 280                 285

Ser Leu Glu Gln Glu Val Gln Gln Gly Asn Ile Phe Ile Val Asp Phe
                290                 295                 300

Glu Leu Leu Asp Gly Ile Asp Ala Asn Lys Thr Asp Pro Cys Thr Leu
       305                 310                 315                 320

Gln Phe Leu Ala Ala Pro Ile Cys Leu Leu Tyr Lys Asn Leu Ala Asn
                       325                 330                 335

Lys Ile Val Pro Ile Ala Ile Gln Leu Asn Gln Ile Pro Gly Asp Glu
                       340                 345                 350

Asn Pro Ile Phe Leu Pro Ser Asp Ala Lys Tyr Asp Trp Leu Leu Ala
                       355                 360                 365

Lys Ile Trp Val Arg Ser Ser Asp Phe His Val His Gln Thr Ile Thr
                370                 375                 380

His Leu Leu Arg Thr His Leu Val Ser Glu Val Phe Gly Ile Ala Met
       385                 390                 395                 400

Tyr Arg Gln Leu Pro Ala Val His Pro Ile Phe Lys Leu Leu Val Ala
                       405                 410                 415

His Val Arg Phe Thr Ile Ala Ile Asn Thr Lys Ala Arg Glu Gln Leu
                       420                 425                 430

Ile Cys Glu Cys Gly Leu Phe Asp Lys Ala Asn Ala Thr Gly Gly Gly
                435                 440                 445

Gly His Val Gln Met Val Gln Arg Ala Met Lys Asp Leu Thr Tyr Ala
                       450                 455                 460

Ser Leu Cys Phe Pro Glu Ala Ile Lys Ala Arg Gly Met Glu Ser Lys
       465                 470                 475                 480

Glu Asp Ile Pro Tyr Tyr Phe Tyr Arg Asp Asp Gly Leu Leu Val Trp
                       485                 490                 495

Glu Ala Ile Arg Thr Phe Thr Ala Glu Val Val Asp Ile Tyr Tyr Glu
                       500                 505                 510

Gly Asp Gln Val Glu Glu Asp Pro Glu Leu Gln Asp Phe Val Asn
                515                 520                 525

Asp Val Tyr Val Tyr Gly Met Arg Gly Arg Lys Ser Ser Gly Phe Pro
       530                 535                 540

Lys Ser Val Lys Ser Arg Glu Gln Leu Ser Glu Tyr Leu Thr Val Val
       545                 550                 555                 560

Ile Phe Thr Ala Ser Ala Gln His Ala Ala Val Asn Phe Gly Gln Tyr
                       565                 570                 575

Asp Trp Ala Ser Trp Ile Pro Asn Ala Pro Pro Thr Met Arg Ala Pro
                       580                 585                 590

Pro Pro Thr Ala Lys Gly Val Val Thr Ile Glu Gln Ile Val Asp Thr
                       595                 600                 605

Leu Pro Asp Arg Gly Arg Ser Cys Trp His Leu Gly Ala Val Trp Ala
                       610                 615                 620

Leu Ser Gln Phe Gln Glu Asn Glu Leu Phe Leu Gly Met Tyr Pro Glu
       625                 630                 635                 640

Glu His Phe Ile Glu Lys Pro Val Lys Glu Ala Met Ala Arg Phe Arg
                       645                 650                 655
```

```
Lys Asn Leu Glu Ala Ile Val Ser Val Ile Ala Glu Arg Asn Glu Asn
                660                 665                 670
Leu Gln Leu Pro Tyr Tyr Tyr Leu Asp Pro Asp Arg Ile Pro Asn Ser
            675                 680                 685
Val Ala Ile
    690

<210> SEQ ID NO 5
<211> LENGTH: 20
<212> TYPE: PRT
<213> ORGANISM: Histidene tab/linker

<400> SEQUENCE: 5

Met Gly Ser Ser His His His His His His Ser Ser Gly Leu Val Pro
1               5                   10                  15
Arg Gly Ser His
            20

<210> SEQ ID NO 6
<211> LENGTH: 29
<212> TYPE: PRT
<213> ORGANISM: B. taurus - 5-LOX - C-terminus

<400> SEQUENCE: 6

Val Ser Val Ile Ala Glu Arg Asn Lys Asn Lys Lys Leu Pro Tyr Tyr
1               5                   10                  15
Tyr Leu Ser Pro Asp Arg Ile Pro Asn Ser Val Ala Ile
            20                  25

<210> SEQ ID NO 7
<211> LENGTH: 29
<212> TYPE: PRT
<213> ORGANISM: S. scrofa - 5-LOX - C-terminus

<400> SEQUENCE: 7

Val Ser Val Ile Ala Glu Arg Asn Lys Asp Lys Lys Leu Pro Tyr Tyr
1               5                   10                  15
Tyr Leu Ser Pro Asp Arg Ile Pro Asn Ser Val Ala Ile
            20                  25

<210> SEQ ID NO 8
<211> LENGTH: 29
<212> TYPE: PRT
<213> ORGANISM: M. mulata - 5-LOX - C-terminus

<400> SEQUENCE: 8

Val Ser Val Ile Ala Glu Arg Asn Lys Lys Lys Gln Leu Pro Tyr Tyr
1               5                   10                  15
Tyr Leu Ser Pro Asp Arg Ile Pro Asn Ser Val Ala Ile
            20                  25

<210> SEQ ID NO 9
<211> LENGTH: 29
<212> TYPE: PRT
<213> ORGANISM: M. musculus - 5-LOX - C-terminus

<400> SEQUENCE: 9

Val Ser Val Ile Ala Glu Arg Asn Lys Asn Lys Lys Leu Pro Tyr Tyr
1               5                   10                  15
Tyr Leu Ser Pro Asp Arg Ile Pro Asn Ser Val Ala Ile
            20                  25
```

<210> SEQ ID NO 10
<211> LENGTH: 29
<212> TYPE: PRT
<213> ORGANISM: M. Auratus - 5-LOX - C-terminus

<400> SEQUENCE: 10

Val Asn Val Ile Ala Glu Arg Asn Lys Asn Lys Lys Leu Pro Tyr Tyr
1               5                   10                  15

Tyr Leu Ser Pro Asp Arg Ile Pro Asn Ser Val Ala Ile
            20                  25

<210> SEQ ID NO 11
<211> LENGTH: 29
<212> TYPE: PRT
<213> ORGANISM: O. cuniculus - 5-LOX - C-terminus

<400> SEQUENCE: 11

Val Ser Val Ile Ala Glu Arg Asn Lys His Lys Lys Leu Pro Tyr Tyr
1               5                   10                  15

Tyr Leu Ser Pro Asp Arg Ile Pro Asn Ser Val Ala Ile
            20                  25

<210> SEQ ID NO 12
<211> LENGTH: 29
<212> TYPE: PRT
<213> ORGANISM: M. domestica - 5-LOX - C-terminus

<400> SEQUENCE: 12

Val Ser Gly Ile Thr Glu Arg Asn Lys Asn Lys Lys Leu Pro Tyr Tyr
1               5                   10                  15

Tyr Leu Ser Pro Asp Arg Ile Pro Asn Ser Val Ala Ile
            20                  25

<210> SEQ ID NO 13
<211> LENGTH: 29
<212> TYPE: PRT
<213> ORGANISM: D. rerio - 5-LOX - C-terminus

<400> SEQUENCE: 13

Ser Lys Thr Ile Lys Asn Arg Asn Glu Gly Lys Lys Leu Pro Tyr Tyr
1               5                   10                  15

Tyr Leu Ser Pro Asp Arg Ile Pro Asn Ser Val Ala Val
            20                  25

<210> SEQ ID NO 14
<211> LENGTH: 29
<212> TYPE: PRT
<213> ORGANISM: S. salar - 5-LOX - C-terminus

<400> SEQUENCE: 14

Ser Ser Ala Ile Lys Ile Arg Asn Glu Gly Lys Lys Leu Pro Tyr Tyr
1               5                   10                  15

Tyr Phe Ser Pro Asp Arg Ile Pro Asn Ser Val Ala Val
            20                  25

<210> SEQ ID NO 15
<211> LENGTH: 29
<212> TYPE: PRT
<213> ORGANISM: H. sapiens - 12R-LOX - C-terminus

<400> SEQUENCE: 15

Ser His Asp Ile Arg Gln Arg Asn Lys Cys Leu Pro Ile Pro Tyr Tyr
1               5                   10                  15

Tyr Leu Asp Pro Val Leu Ile Glu Asn Ser Ile Ser Ile
            20                  25

<210> SEQ ID NO 16
<211> LENGTH: 29
<212> TYPE: PRT
<213> ORGANISM: H. sapiens - E3-LOX - C-terminus

<400> SEQUENCE: 16

Ser Arg Asp Ile Gln Glu Arg Asn Gln Gly Leu Ala Leu Pro Tyr Thr
1               5                   10                  15

Tyr Leu Asp Pro Pro Leu Ile Glu Asn Ser Val Ser Ile
            20                  25

<210> SEQ ID NO 17
<211> LENGTH: 29
<212> TYPE: PRT
<213> ORGANISM: H. sapiens - 15B-LOX - C-terminus

<400> SEQUENCE: 17

Ser Arg Gly Ile Gln Glu Arg Asn Gln Gly Leu Val Leu Pro Tyr Thr
1               5                   10                  15

Tyr Leu Asp Pro Pro Leu Ile Glu Asn Ser Val Ser Ile
            20                  25

<210> SEQ ID NO 18
<211> LENGTH: 29
<212> TYPE: PRT
<213> ORGANISM: H. sapiens - 15A-LOX - C-terminus

<400> SEQUENCE: 18

Asp Lys Glu Ile Glu Ile Arg Asn Ala Lys Leu Asp Met Pro Tyr Glu
1               5                   10                  15

Tyr Leu Arg Pro Ser Val Val Glu Asn Ser Val Ala Ile
            20                  25

<210> SEQ ID NO 19
<211> LENGTH: 29
<212> TYPE: PRT
<213> ORGANISM: O. cuniculus - 15-LOX - C-terminus

<400> SEQUENCE: 19

Asp Lys Glu Ile Glu Val Arg Asn Glu Lys Leu Asp Ile Pro Tyr Glu
1               5                   10                  15

Tyr Leu Arg Pro Ser Ile Val Glu Asn Ser Val Ala Ile
            20                  25

<210> SEQ ID NO 20
<211> LENGTH: 29
<212> TYPE: PRT
<213> ORGANISM: H. sapiens - 12S-LOX - C-terminus

<400> SEQUENCE: 20

Glu Lys Glu Ile Thr Ala Arg Asn Glu Gln Leu Asp Trp Pro Tyr Glu
1               5                   10                  15

Tyr Leu Lys Pro Ser Cys Ile Glu Asn Ser Val Thr Ile
            20                  25

<210> SEQ ID NO 21
<211> LENGTH: 29

```
<212> TYPE: PRT
<213> ORGANISM: homomalla - 8R-LOX - C-terminus

<400> SEQUENCE: 21

Ser Lys Lys Ile Lys Gln Arg Asn Glu Asn Leu Glu Val Pro Tyr Ile
1               5                   10                  15

Tyr Leu Leu Pro Glu Arg Ile Pro Asn Gly Thr Ala Ile
            20                  25
```

US 8,877,476 B2

SOLUBLE AND STABLE HUMAN 5-LIPOXYGENASE

This is the United States national stage of international application PCT/US2011/038492, international filing date May 31, 2011, which claims the benefit of the filing date of provisional U.S. application Ser. No. 61/350,197, filed 4 Jun. 1, 2010, under 35 U.S.C. §119(e).

This invention was made with government support under grant No. 0818387 awarded by the National Science Foundation and under grant No. GM-15431 awarded by the National Institutes of Health. The government has certain rights in the invention.

TECHNICAL FIELD

This invention pertains to soluble and stable forms of 5-lipoxygenase ("5-LOX"), suitable for a number of applications, including, but not limited to, high throughput screening of 5-LOX inhibitors, resolution of the crystal structure of 5-LOX, structural analysis of the 5-LOX active site, designing inhibitors based on the three-dimensional structure of the 5-LOX active site, and synthesis of LTA4.

BACKGROUND ART

Lipoxygenases are a family of non-heme iron dioxygenases that catalyze the stereo- and regio-specific formation of fatty acid hydroperoxides from polyunsaturated fatty acids (35, 36). In addition to 5-LOX, which catalyzes the peroxidation of arachidonic acid (AA) at the C5 position, mammalian lipoxygenases that form the 12-, 15- and 8-hydroperoxide products of AA oxygenation (hydroperoxyeicosatetraenoic acid, HPETE) have also been described. Their products are converted to other oxylipins with diverse roles in biology (see (35)). Lipoxygenases are also widely distributed throughout the plant kingdom (35), but the substrates for the plant enzymes are generally the 18 carbon linoleic and linolenic acids rather than the 20 carbon AA recognized by animal enzymes. The first step of a LOX-catalyzed reaction is hydrogen abstraction at the central carbon of a pentadiene moiety by the activated $Fe^{3+}$ (37) to produce a free radical intermediate which is oxygenated two carbons removed from the position of hydrogen abstraction. Active site control of regio-specificity is determined by which pentadiene of the substrate is positioned for attack, and whether $O_2$ has access to carbon $C_{-2}$ or $C_{+2}$. Animal lipoxygenases are named according to their product specificity; while AA is the substrate for all of them, the position and stereochemistry of the hydroperoxy group introduced is specific for a given isoform. 5-LOX catalyzes both the dioxygenation of an unsaturated fatty acid to its hydroperoxy derivative, the reaction common to all lipoxygenases, and the subsequent transformation of the 5-hydroperoxyeicosatetraenoic acid (5-HPETE) to leukotriene A4, in which one of the oxygen atoms of the hydroperoxide ends up in an epoxide. The first reaction requires abstraction of hydrogen at C7, while the second reaction requires abstraction of the hydrogen at C10.

In the human body, 5-LOX is used to produce pro-inflammatory leukotrienes, which are potent lipid mediators of the inflammatory response. As stated above, 5-LOX catalyzes a two step transformation of (1) arachidonic acid (AA) at the 5-position to yield 5-hydroperoxyeicosatetraenoic acid (5-HPETE), and then (2) 5-HPETE to leukotriene A4. Leukotrienes are potent lipid mediators of the inflammatory response, including the response involved in asthma. Over the last 25+ years, substantial progress has been made in understanding how leukotrienes exert their effects, and a broader appreciation for the numerous biological processes that leukotrienes mediate has resulted. For example, 5-LOX has been linked to development of heart disease, stroke and atherosclerosis.

Leukotrienes (LT) and lipoxins are potent mediators of the inflammatory response derived from arachidonic acid (AA). When leukocytes are activated, arachidonic acid is released from the nuclear membrane by the action of cytosolic phospholipase $A_2$ and binds five-lipoxygenase-activating protein (FLAP). The increased $Ca^{2+}$ concentration of the activated cells simultaneously promotes translocation of 5-LOX to the nuclear membrane where it acquires its substrate from FLAP (1, 2). Arachidonic acid (AA) is converted to leukotriene ($LTA_4$) in a two-step reaction which produces the 5S-isomer of hydroperoxyeicosatetraenoic acid (5S-HPETE) as an intermediate (3, 4).

Work with the plant enzymes has afforded tremendous insight into the mechanism of hydrogen abstraction by the active site iron, but the basis for regio-specificity of the animal enzymes is still unclear. The 1.85 Å resolution structure of an 8R-lipoxygenase has been described (7, 10). In addition, there is a structure available for the 15S-enzyme from rabbit reticulocytes (11, 12).

Regulatory mechanisms that provide the transient activities associated with temporal control of cellular events include targeted degradation, phosphorylation, and allosteric control of enzyme activities. Auto-inactivation that is a consequence of intrinsic protein (in)stability can also have a role in temporal control of protein function. For example, the relative instability of the tumor suppressor protein p53, relative to its orthologs such as p73, has been proposed to a have a functional role (9).

Auto-inactivation has been proposed to play an important regulatory role in mammalian 5-lipoxygenase (5). As mentioned above, in mammals LOX products are the precursors of potent lipid mediators of the inflammatory response; thus an overproduction of the signaling compounds is detrimental to the organism. Enzyme lability, whether a consequence of turnover or non-turnover-based inactivation, serves as an auto-shutoff valve, an innate "programmed obsolescence." In contrast, the 8R-LOX from *Plexaura homomalla* is remarkably stable, perhaps an indication that constitutive production of LOX products is beneficial to the soft coral (7). Human 5-LOX and *P. homomalla* 8R-LOX represent two extremes of lipoxygenases. While these enzymes share 40% sequence identity, and consequently a protein fold, they differ significantly in their inherent stabilities, with 5-LOX a notoriously unstable enzyme, and the 8R-enzyme remarkably robust. Yet the enzymes recognize the same substrate, utilize the same catalytic machinery, and perform a common chemical transformation. Furthermore, both are targeted to the membrane in a $Ca^{2+}$-dependent fashion. The $Ca^{2+}$-binding amino acids, as well as putative membrane insertion loops, are shared by these two lipoxygenases, but absent in all other lipoxygenase isoforms.

Purified, human 5-LOX is unstable, having a half-life as short as 10-hours at 4° C. (8). In addition, its low solubility and "stickiness" frustrates handling of the enzyme. Native 5-LOX variants have a tendency to "clump" when placed in aqueous solutions, which leads to wasteful residues being left on containers, such as glass beakers. A soluble and/or stable form of human 5-LOX is highly desirable.

DISCLOSURE OF INVENTION

By making several key modifications to the human 5-LOX peptide sequence, we have successfully produced a soluble and stable form of 5-LOX, which retains a robust enzymatic activity. The amino acid sequence of the native, human 5-LOX (SEQ ID NO: 1) as found in vivo is shown in FIG. 1, and the amino acids that were changed for all our new forms of 5-LOX are bolded and underlined. The amino acid sequence of a more soluble 5-LOX ("Sol-5-LOX") is shown in FIG. 2 as SEQ ID NO:2, and the added or changed amino acids from native 5-LOX are bolded and underlined. The amino acid sequence of our soluble and stable form of human 5-LOX, "Octa-LOX" or "Stable-5-LOX", (SEQ ID NO: 3) is shown in FIG. 3, and again the added or changed amino acids from native 5-LOX are bolded and underlined. We have also made an additional change to Stable-5-LOX to mimic the enzyme in a constitutively phosphorylated state and called this one "S663D-Stable-5-LOX". This sequence (SEQ ID NO: 4) is shown in FIG. 4, with the added or changed amino acids from native 5-LOX bolded and underlined. In addition we have used Stable-5-LOX to obtain the crystal structure at 2.4 Å resolution, and diagram the active site of 5-LOX. These new forms of 5-lipoxygenase are thus suitable for a number of applications, including, but not limited to, high throughput screening of 5-LOX inhibitors, resolution of the crystal structure of 5-LOX, structural analysis of the 5-LOX active site, designing inhibitors based on the three-dimensional structure of the 5-LOX active site, and synthesis of LTA4.

BRIEF DESCRIPTION OF THE DRAWINGS

FIG. 1 gives the amino acid sequence (SEQ ID NO: 1) of native human arachidonate 5-lipoxygenase after cleavage of the initial amino acid, methionine (M), as occurs in vivo. The amino acids that were modified in one or more of the new forms of 5-LOX are bolded and underlined.

FIG. 2 gives the amino acid sequence (SEQ ID NO: 2) of the more soluble form of 5-LOX, Sol-5-LOX, with the amino acids that are different from the native 5-LOX shown as bolded and underlined.

FIG. 3 gives the amino acid sequence (SEQ ID NO: 3) of the more soluble and stable form of 5-LOX, Stable-5-LOX, with the amino acids that are different from the native 5-LOX shown as bolded and underlined.

FIG. 4 gives the amino acid sequence (SEQ ID NO: 4) of the more soluble and stable form of 5-LOX, Stable-5-LOX, with a change at amino acid 663 to mimic the enzyme in a phosphorylated state (S663D-Stable-5-LOX, and again the amino acids that are different from the native 5-LOX shown as bolded and underlined.

FIG. 5 shows the alignment of the 29 amino acids of the C-terminal sequences of 5-LOX from 10 different species (the top 10; SEQ ID NO: 1 (the last 29 amino acids); SEQ ID NOS: 6-14), and of non-5-LOXs (the bottom 7; SEQ ID NOS: 15-21). The lysine-rich area of the 5-LOX sequences is bolded and underlined. The highly conserved leucine residue of the non-5-LOX sequences is also bolded and underlined.

FIG. 12A is a schematic representation showing the positioning of helix α2 is unique in 5-LOX compared to comparable sections of 15-LOX and 8R-LOX. Conserved aromatic amino acids (F169, W201) that flank the region are in stick rendering. F177 and Y181 that make up the "cork" that helps define the active site are in stick. The catalytic iron is shown as a sphere near the center.

FIG. 12B is a schematic representation of a full overlay of the three structures for 5-LOX, 15-LOX and 8R-LOX in which it is apparent that, with the exception of the helix α2, the secondary structural elements in the enzymes are conserved. The box indicates the region amplified in FIG. 12A.

FIG. 13A shows the active site cavity of 15-LOX (2P0M) calculated with CastP (30) as the lighter grey area. Invariant Leu and Ile side chains (362, 367, 400, 408 and 597) are in stick rendering. The 5-LOX "FY cork", F177 and Y181, a darker grey, is superposed on the 15-LOX cavity and plugs the entrance.

FIG. 13B shows the active site cavity of Stable-5-LOX calculated with CastP (30) in an equivalent orientation of the active site cavity to that seen for 15-LOX in FIG. 13A. Invariant Leu and Ile side chains (368, 373, 406, 414, and 607) are in stick rendering. Note the similarity of the positions of these amino acids to their counterparts in 15-LOX in FIG. 13A. Iron coordination sphere amino acids (367, 372, 550, 554, and 673) are also seen in stick rendering, and the iron an orange sphere.

FIG. 13C shows the active site cavity of Stable-5-LOX calculated with CastP (30), with the 5-LOX amino acids (147, 177, 181, 364, 407, 420, 421, 432, 599, 600, 603, and 606) that contribute to the active site cavity in stick rendering. Entry into this cavity requires a conformational change.

MODES FOR CARRYING OUT THE INVENTION

Figure 6A:
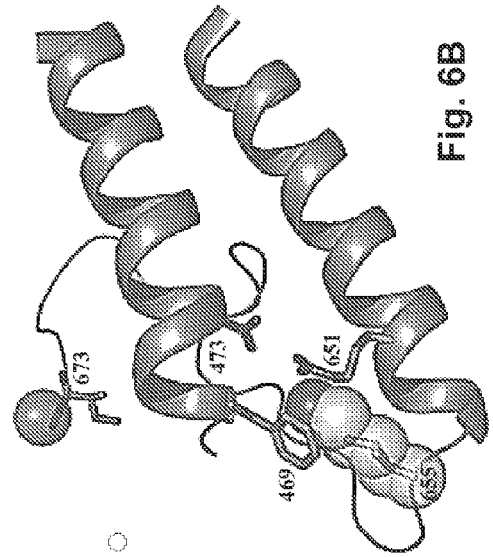
FIG. 6A is a schematic representation of the superposition of the C-terminal regions of the structures of 15-lipoxygenase, 8R-lipooxygenase, and Stable-5-lipoxygenase. The C-terminal segment that leads to the catalytic Fe emanates from the helix which terminates at amino acid 655 (native human 5-LOX numbering). Highly conserved amino acids (Leu, Phe/Tyr) and an invariant salt link (473Asp-651Arg) are depicted in stick rendering.

We made the following modifications, principally replacing hydrophobic amino acids with less hydrophobic amino acids, to confer greater solubility relative to that of the Native 5-LOX. FIG. 1 shows the native human 5-LOX sequence (SEQ ID NO: 1) as it exists in vivo with 673 amino acids after the cleavage of the initial methionine (M) amino acid. All references to amino acid residues are made to this sequence. The sequence has also been given with 674 amino acids by including the initial methionine as residue 1, which would add one residue placement to all residue numbers stated therein. However, the initial M is included in the sequences that we modified below.

Initially, we engineered a soluble form of human 5-LOX by removal and substitution of various regions in the 5-LOX protein. This new form was called "Sol-5-LOX" (SEQ ID NO: 2; FIG. 2). The following changes were made to native human 5-LOX (SEQ ID NO:1; FIG. 1) to make Sol-5-LOX (SEQ ID NO: 2; FIG. 2) counting from the N-terminus of SEQ ID NO: 1: (1) amino acids 13-14 (i.e., Tryptophan and Phenylalanine) were replaced with Glutamic acid and Histidine; (2) amino acids 40-44 (i.e., Proline. Phenylalanine, Tyrosine, Asparagine, and Aspartic acid) were replaced with Glycine and Serine; (3) amino acids 75-76 (i.e., Tryptophan and Leucine) were replaced with Glycine and Serine; and (4) amino acids 240 and 561 (both Cysteine) were replaced with Alanine. The amino acids that were to be modified are shown in the native human 5-LOX sequence in FIG. 1 as bolded and underlined amino acids. The sequence (SEQ ID NO: 2) for Sol-5-LOX is shown in FIG. 2 with the differences from the native human 5-LOX shown in bold and underlined. All mutations were made by whole plasmid polymerase chain reaction (PCR), as described below. Primers for single-site mutations were designed to introduce a restriction site that was used to identify the plasmids carrying the mutation. Expression of this protein (Sol-5-LOX) yields ~10 mg/liter culture. Importantly, Sol-5-LOX, unlike its native counterpart, can be purified without detergents.

Next, we introduced a "stabilizing feature" into the mutant Sol-5-LOX. We exchanged the tri-Lys peptide in 5-LOX for the sequence found in the 8R-enzyme. Replacing amino acids 653-655 (i.e., KKK or Lysine-Lysine-Lysine), as numbered in FIG. 1, with its counterpart in 8R-LOX (i.e., Glutamic acid, Asparagine, and Leucine) yielded an enzyme ("Stable-5-LOX"; SEQ ID NO: 3; FIG. 3) with greatly enhanced catalytic activity (~50 fold greater than that of Sol-5-LOX), and a significantly longer half life. The sequence of Stable-5-LOX (SEQ ID NO: 3) is shown in FIG. 3, with the differences from native human 5-LOX shown as bolded and underlined. The half life of native 5-LOX is 10 h [8], whereas the half life of Stable-5-LOX is 1 week (both at 4° C.). We believe that making this change to the native 5-LOX (in absence of the solubility mutations of Sol-5-LOX) would also make native 5-LOX more stable. Without wishing to be bound to this theory, it is believed that the most important replacement for increased stability is of amino acid 655, Lysine, which has a positive charge, with an amino acid having a non-positive charge (e.g., not Lysine or Arginine). Stable-5-LOX can be concentrated to 12 mg/ml, in contrast to 2 mg/ml for Sol-5-LOX. Thus a soluble and stable form of human 5-LOX ("Stable-5-LOX") was made and was used for structural analysis of the 5-LOX active site and for determining the crystal structure of 5-LOX. Stable-5-LOX can also be used for a number of applications, including, but not limited to, high throughput screening of 5-LOX inhibitors, designing inhibitors based on the three-dimensional structure of the 5-LOX active site, and synthesis of LTA4.

An additional modification of the amino acid sequence of native human 5-LOX was to add a tag and "linker" sequence of amino acids at the N-terminus. This tag and linker was added to both Sol-5-LOX and Stable-5-LOX. A commercially available plasmid (pET-14b) was purchased which encodes a His-Tag® and "linker" in the plasmid (EMD Chemicals. Inc., Madison, Wis.). The sequence consists of the following 20 amino acids: MGSSHHHHHHSSGLVPRGSH (SEQ ID NO:5). This addition of a tag and linker has several uses including, but not limited to: aiding in the isolation and purification of the polypeptide (especially the histidine (HHHHHH) sequence), acting as a means to immobilize the operable 5-LOX enzyme to the stationary phase of a column or other screening device, or aiding in distinguishing between the engineered protein and the "native" type using commercially available anti-bodies that bind to HHHH. The HHH-HHH sequences also aid in crystallization.

The amino acid sequence of the preferred embodiment of Stable-5-LOX (SEQ ID NO: 3) is shown in FIG. 3. Using this soluble and stable 5-LOX, we were able to determine the crystal structure of 5-LOX, using the methods discussed below. The high resolution structure characterized by the coordinates was deposited at the Protein Data Bank (PDB) ID: 3O8Y and is available through the PDB internet website. Knowledge of the crystal structure was used to characterize the active site and can be used to design and to test inhibitors that bind the active site of 5-LOX.

We produced another embodiment of Octa-LOX, so called "S663D-Stable-5-LOX" (SEQ ID NO: 4; FIG. 4) to mimic the enzyme in a constitutively phosphorylated state. The 663rd amino acid, Serine, of human 5-LOX (SEQ ID NO: 1) was replaced with Aspartic acid. The position of this change is not close to the active site, and the change is useful for understanding how the enzyme works. This amino acid change converted the enzyme from a 5-LOX to a 15-LOX. The sequence of S663D-Stable-5-LOX (SEQ ID NO: 4) is shown in FIG. 4, with the differences from native human 5-LOX shown as bolded and underlined.

This invention relates not only to the modified sequences as shown in SEQ ID NO: 2. SEQ ID NO:3, and SEQ ID NO: 4 as described in this specification, but also to proteins having modifications to such a sequence resulting in an amino acid sequence having the same function (i.e., an enzyme whose activity and stability is similar to that reported herein), and about 60-70%, preferably 90% or greater, homology to the sequence of the amino acid sequence as described, more preferably about 95% or greater homology, particularly in conserved regions. "Homology" as used here means identical amino acids or conservative substitutions (e.g. acidic for acidic, basic for basic, polar for polar, nonpolar for nonpolar, aromatic for aromatic). The degree of homology can be determined by simple alignment based on programs known in the art, such as, for example, GAP and PILEUP by GCG, or the BLAST software available through the NIH internet site. Most preferably, a certain percentage of "homology" would be that percentage of identical amino acids.

Example 1

Materials and Methods

Construction of Plasmid for Protein Expression.

The 5-LOX insert in pCR2.1 was amplified by the polymerase chain reaction, cloned into pET28b (EMD Chemicals, Inc., Madison, Wis.), and then subcloned into pET14b for leaky expression. Mutations were constructed using whole plasmid PCR as described (7). When possible, primers were constructed to contain silent mutations that facilitated screening of plasmids. Small scale expression to assess expression levels and solubility of the various mutant 5-LOXs was carried out by autoinduction (30).

Protein Expression and Purification.

Rosetta 2 (DE3) cells (EMD Chemicals, Inc.) harboring the pET14b-Stable-5-LOX or pET14b-Sol-5-LOX plasmids were grown in Terrific Broth (Scientific Strategies, Yukon, Okla.) containing 34 µg ml$^{-1}$ chloramphenicol and 100 µg ml$^{-1}$ ampicillin at 37° C. for 3.5 h and then shifted to 20° C. for an additional 26 h. Cells were harvested, pelleted, and frozen at −80° C. Cells were resuspended in Bugbuster (EMD Chemicals, Inc.; 2 ml/g) supplemented with 1 µM Pepstatin, 100 µM PMSF, and DNaseI (2 Kunitz/g). All reagents are from Sigma-Aldrich Corp. (St. Louis, Mo.) unless otherwise indicated. The suspension was lysed in a French pressure cell and centrifuged at 40,000×g (30 min). Clarified lysate was applied to a HisTrap 5 ml Ni$^{2+}$ Sepharose column (GE Healthcare, Piscataway, N.J.) equilibrated in 50 mM Tris (pH 8.0), 500 mM NaCl, 20 mM imidazole and eluted with a linear gradient to 50 mM Tris pH 8.0, 500 mM NaCl, 200 mM imidazole on an AKTA FPLC (GE Healthcare). The peak fractions were concentrated in an Amicon Ultra 30K (Millipore) to a final volume of 2 ml. The concentrated protein was applied to a HiLoad 16/60 Superdex 200 pg (GE Healthcare), equilibrated in 20 mM Tris pH 8.0, 150 mM NaCl, 5 mM TCEP-HCl, and eluted as both a dimer and monomer. All experiments were performed with monomeric enzyme: there are no contacts in the crystal lattice consistent with a stable dimer. Protein purity was checked by SDS-PAGE. Enzyme activity was monitored with a UV-spectrophotometer with diode array detector (Agilent Technologies, Santa Clara, Calif.), and protein was frozen in liquid N$_2$.

Product Assays.

Figure 6B:
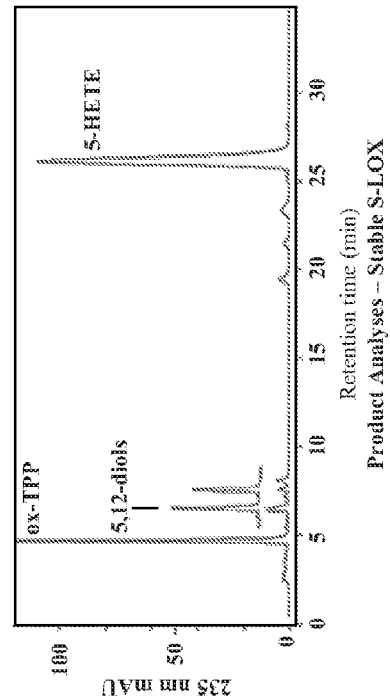
FIG. 6B is a schematic representation of the turn at the end of the terminal helix. The 5-LOX specific Lys (substituted in Stable-5-LOX with Leu) is modeled at position 655 as its most common rotamer (transparent sphere rendering). As positioned, it would interfere with the invariant salt-link and cation-π interactions. All figures were generated with PyMOL, a user-sponsored molecular visualization system on an open-source foundation (Schrödinger, L.L.C., Rockville, Md.).
Figure 6C:
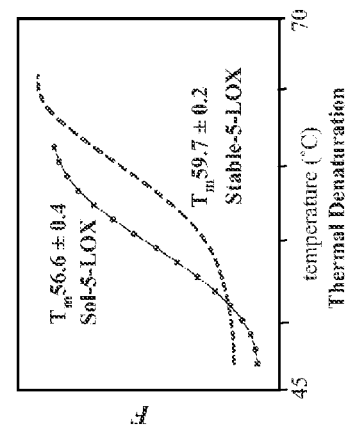
FIG. 6C shows the thermal denaturation graphs of Stable-5-LOX and the parent enzyme Sol-5-LOX. Fluorescence (F) was monitored as a function of temperature. $T_m$ (with s.d.) was 56.6(±0.4) and 59.7(±0.2)° C. for Sol-5-LOX and Stable-5-LOX, respectively.
Figure 6D:
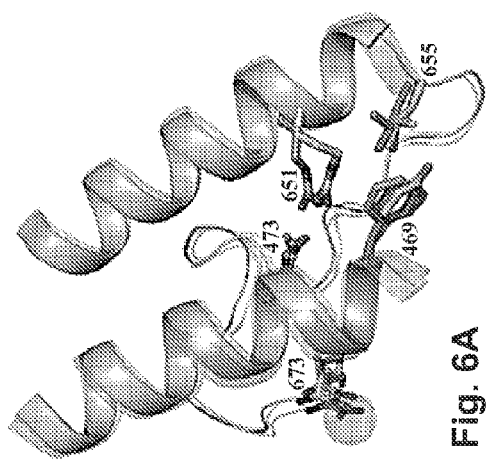
FIG. 6D is an HPLC chromatogram of the products of Stable-5-LOX showing the production of both 5-HETE (5-HPETE reduced by the addition of triphenylphosphine. TPP) and Leukotriene $A_4$ hydrolysis products (5,12 diols).
Figure 8:
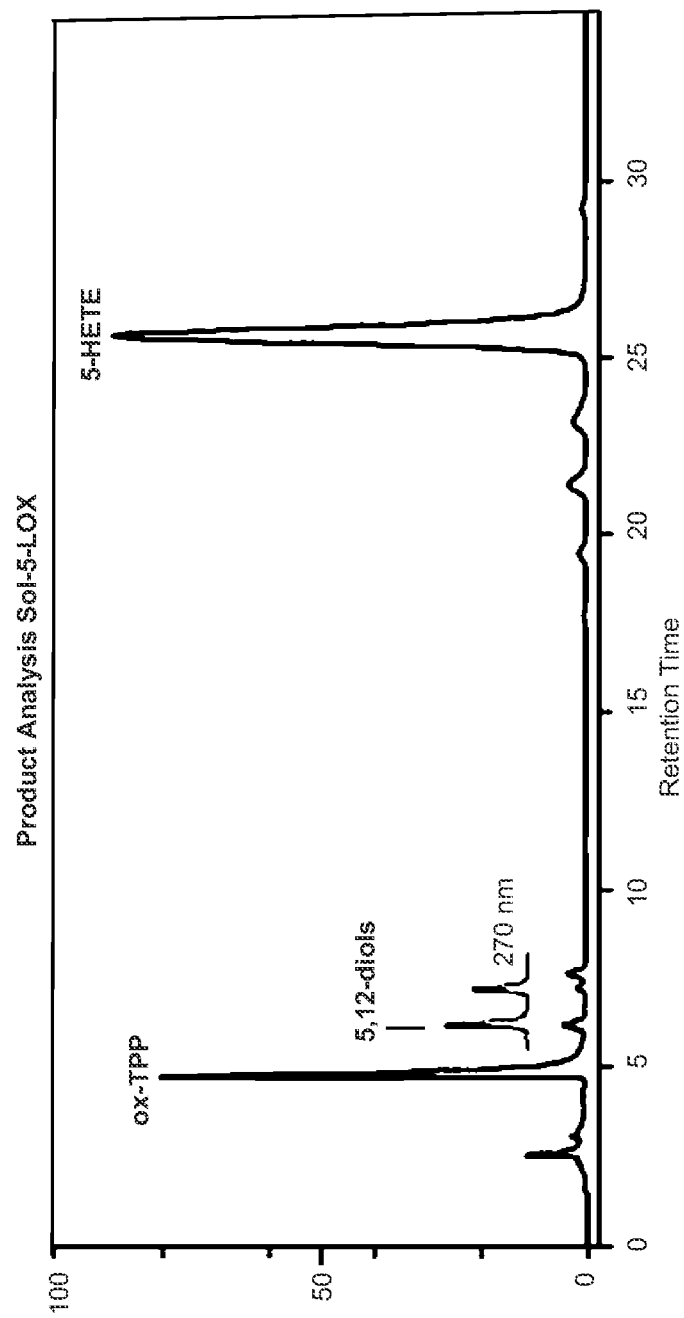
FIG. 8 is an HPLC chromatogram of the products of Sol-5-LOX showing the production of both 5-HETE (5-HPETE reduced by the addition of triphenylphosphine, TPP) and Leukotriene $A_4$ hydrolysis products (5,12 diols).

Incubations were conducted in 0.5 ml 0.1 M Tris pH 7.5 containing 150 mM NaCl and 1 mM CaCl$_2$ with 1-20 µg/ml 5-LOX enzyme. The reaction was initiated by addition of arachidonic acid (10-100 µM) added in 1-5 µl ethanol and monitored by UV spectroscopy until completion of reaction (5-10 min). Products were extracted by adjusting the solution to ~pH 4 by addition of 50 µl 1 M KH$_2$PO$_4$ plus 5 µl 1N HCl and vigorous mixing with two volumes of dichloromethane. After a brief centrifugation to clear the phases, the lower organic layer was collected, washed twice with 0.5 ml water, taken to dryness under a stream of nitrogen, and then dissolved in a small volume of methanol for storage at −20° C. prior to HPLC. Reversed-phase HPLC was carried out using Agilent 1100 series equipment with a Waters C18 Symmetry column (25×0.46 cm), a solvent of acetonitrile/water/glacial acetic acid (60:40:0.01, v/v/v) or methanol/water/glacial acetic acid (80:20:0.01, v/v/v), a flow rate of 1 ml/min, with UV monitoring at 205 nm, 220 nm, 235 nm and 270 nm. The chirality of the product was confirmed as 5S: Mobile phase hexane/methanol 100:2; 1 ml/min; Chiralpak AD column (4.6×250 mm). The HETEs were made into the methyl esters before chiral analysis using ethereal diazomethane. The results for Sol-5-LOX are shown in FIG. 8; and the results for Stable-5-LOX are shown in FIG. 6D.

Enzyme Assays.

Figure 7:
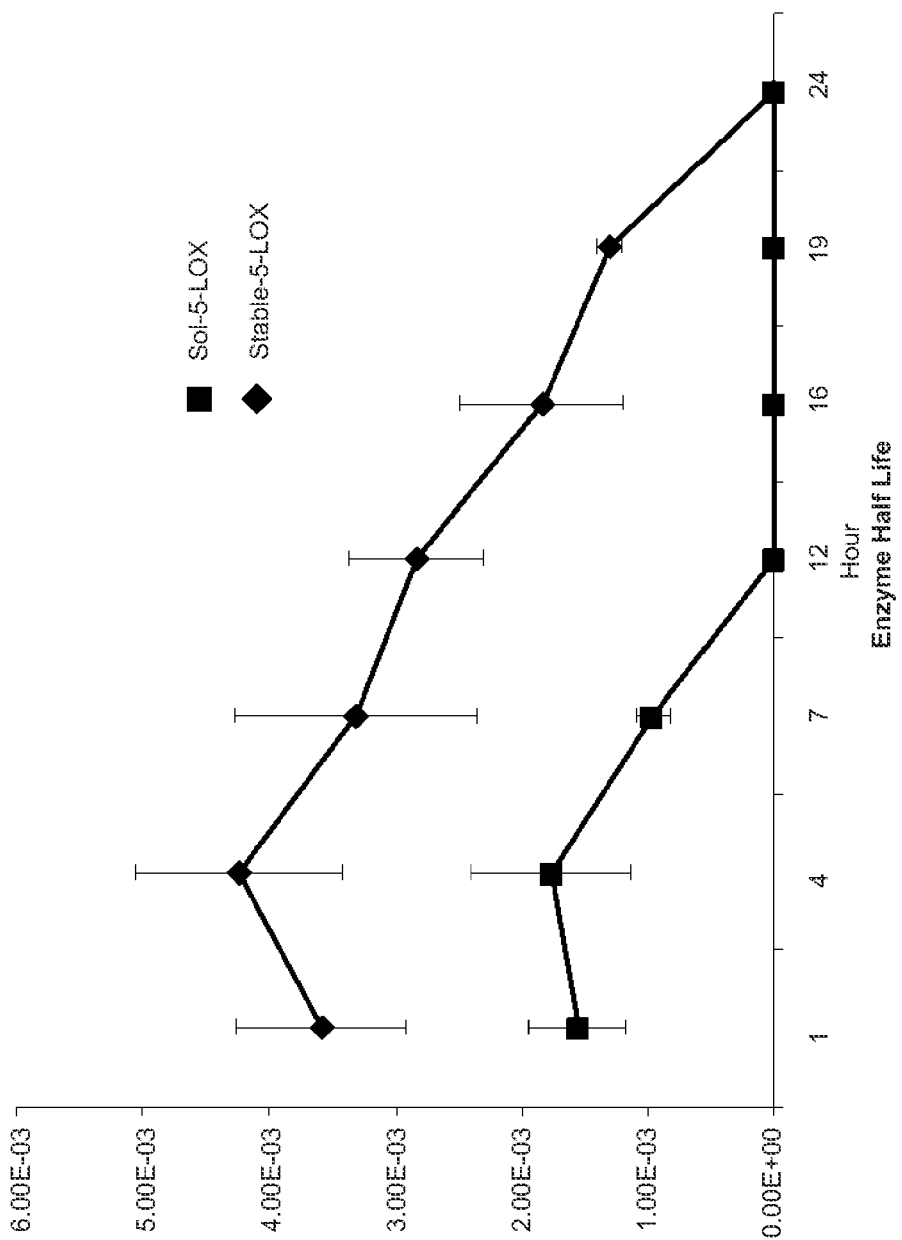
FIG. 7 shows the enzyme half-life for both Sol-5-LOX and Stable-5-LOX by monitoring enzyme activity (($\Delta A_{238}$) over the course of 24 hrs at 37° C.

Sol-5-LOX and Stable-5-LOX were assayed over the course of 24 hrs by monitoring the absorbance at 238 nm in an Agilent 8453 Diode Array Spectrophotometer. Enzyme was incubated at 37° C. in 20 mM Tris-HCl (pH 8.0), 150 mM NaCl, 5 mM TCEP. Assays were performed in 20 mM Tris-HCl (pH 7.5), 150 mM NaCl, 0.5 mM CaCl$_2$. The reaction was initiated by the addition of 65 µM arachidonic acid (AA) and monitored at room temperature. Enzyme assays for K$_M$ determination were performed in similar conditions, except that the concentration of AA varied from 1.5 to 26 µM. The K$_M$ was calculated by non-linear regression analysis of a plot of velocity vs. substrate concentration (Sigma Plot 9). The data shown in FIG. 7 represent the results of duplicate experiments.

Melting Curves.

Melting temperature assays were performed according to the protocol described by Ericsson et al. (31) Protein was diluted to 1 µM in a final volume of 150 µl 5×SYPRO® Orange protein stain (Invitrogen, Carlsbad, Calif.). Samples were aliquoted in triplicate volumes of 40 µl in a 96-well reaction plate. The plate was subjected to a linear thermal shift from 5 to 94° C. in one degree increments in a 7500 Fast Real-Time PCR System (Applied Biosystems, Branchburg, N.J.). The SYBR Green cutoff filter was used for fluorescence detection of denaturing protein-SYPRO® Orange binding. The resulting data were exported to Sigma Plot 9, and the sigmoidal part of the curve was averaged for each triplicate. The averaged curves were subsequently fit to a four parameter sigmoidal equation. The T$_m$ values reported are the results of four independent experiments, each in triplicate, with multiple protein preparations. Results for both Sol-5-LOX and Stable-5-LOX are shown in FIG. 6C.

Crystallization.

Stable-5-LOX monomer crystals were grown by hanging-drop vapor diffusion at 295 K by mixing 1 µl protein (8 mg/ml) and 2 µl reservoir solution containing 8-10% Tacsimate pH 6.0 (Hampton Research). The crystals were soaked in 70% Tacsimate pH 6.0 and then frozen for shipment and data collection. Crystals belong to space group P2$_1$ (a=54.99, b=202.67, c=76.47 Å, β=109.35°); there are two monomers in the asymmetric unit.

Structure Determination.

Diffraction data were collected at 100 K at the NE-CAT beamline 24-ID-E at the Advanced Photon Source, Argonne, Ill. Data were processed with Xia2. A search model based on the 8R-lipoxygenase structure (40% sequence identity) was prepared with Chainsaw. Molecular replacement was performed with Phaser (Z-scores 31.47, 29.24). Initial refinement of the Chainsaw model (which retains atoms common to 8R- and 5-LOX) resulted in an R$_{free}$=0.39 in REFMAC, while that of the equivalent polyalanine model reached 0.45. Chainsaw, Phaser and REFMAC are all part of the CCP4 suite (4). Manual model building was performed with Coot (5). Refinement was continued in Phenix (6) with non-crystallographic symmetry restraints, individual atomic displacement factors (B-factors), and automatic water picking. The final model has R$_{work}$ and R$_{free}$ values of 18.0 and 21.0, respectively. Illustrations were prepared with PyMOL. Table 1 gives the Data Collection and refinement statistics. The high resolution crystal structure of 5-LOX characterized by the coordinates was deposited at the Protein Data Bank ID: 3O8Y and is available through the PDB internet website.

Example 2

More Detailed Stable-5-LOX Preparation

A commercially available plasmid (pET-14b) was purchased that included a His-Tag® and linker (EMD Chemicals, Inc.). The plasmid was constructed to also contain the gene for human 5-lipoxygenase with the following mutations: Δ40-44 GS; C561A/C240A; W13E/F14H; W75G/L76S; and Δ653-655 ENL. The new plasmid was transformed into Rosetta 2 cells (EMD Chemicals, Inc.), and the cells plated onto MDAG supplemented with ampicillin (100 µg/ml) and Chloramphenicol (34 µg/ml). The MDAG and other media used is as previously described (30). Overnight colonies were picked and used to inoculate 25 ml Luria Broth (LB) in a 125 ml flask. A volume of 5 ml of the overnight culture was used to inoculate 0.5 L Terrific Broth (TB) in 2.0 L flasks. The flasks were incubated for 3.5 hours @ 37° C. with shaking at 220 rpm. The growth temperature was then shifted to 20° C., and the cultures were grown for an additional 26 hrs.

Three liters of culture yielded about 56 gm pellets after centrifugation at 5000 rpm (SLA-1500 rotor) for 15 min. The pellets were suspended in 112 ml of Bugbuster® (EMD Chemicals, Inc.) with the addition of 50 µl of Pepstatin (1 mM), DNase 1 (100 Kunitz units) and phenylmethylsulfonyl fluoride (PMSF) (6 mg). The mixture was stirred for ~20 min at 4° C., pressed with a French Press above 16,000 PSI, and then centrifuged 30 min at 42,000×g. The supernatant was collected, and 1 part Buffer B (50 mM Tris pH 8.0, 500 mM NaCl, 200 mM Imidazole pH 8.0) was added to 9 parts supernatant. The supernatant was then applied to a 5 ml HisTrap™ HP column (GE Healthcare) and eluted with a linear gradient going from Buffer A (50 mM Tris pH 8.0, 500 mM NaCl, 20 mM Imidazole pH 8.0) to Buffer B (50 mM Tris pH 8.0, 500 mM NaCl, 200 mM Imidazole pH 8.0), and monitored absorbance at 280 nm.

The largest peak was collected and concentrated to approximately 4 ml. Two batches (2 runs at 2 ml each) were then applied to a HiLoad™ 16/60 Superdex™ 200 Size Exclusion Column (SEC) (GE Healthcare). The SEC Buffer used was 20 mM Tris, 150 mM NaCl, 5 mM tris (2-carboxyethyl)phosphine (TCEP), pH 8.0. Stable-5LOX eluted as a dimer at 71 ml and as a monomer at 80 ml.

Example 3

Crystal Structure and Active Site of Stable-5-LOX

As discussed in Materials and Methods, a crystal structure was resolved for Stable-5-LOX. The data collection and refinement statistics for the resolution are shown in Table 1. The high resolution structure characterized by the coordinates was deposited at the Protein Data Bank (ID: 3O8Y) and is available through the PDB internet website. As shown below, knowledge of the crystal structure was used to characterize the active site and present the active site in schematic drawings. The structure of the active site can be used to design and test inhibitors that bind the active site of 5-LOX.

TABLE 1

Data Collection and refinement statistics

| | Stable-5-LOX |
|---|---|
| Data Collection | |
| Space group | $P2_1$ |
| Cell dimensions | |
| a, b, c (Å) | 55.17, 202.89, 76.80 |
| α, β, γ(°) | 90.00, 109.56, 90.00 |
| Wavelength | 0.97916 |
| Resolution (Å) | 51.99-2.39 (2.45-2.39) |
| $R_{p.i.m.}$ | 0.143 (0.670) |
| I/σI | 6.9 (2.4) |
| Completeness (%) | 99.9 (100.0) |
| Redundancy | 3.7 (3.6) |
| Wilson B factor | 31.20 |
| Refinement | |
| Resolution (Å) | 40.77-2.39 (2.47-2.39) |
| No. reflections | 59131 (5238) |
| $R_{work}/R_{free}$ | 18.24/20.97 (24.79/28.40) |
| No. atoms | |
| Protein | 10937 |
| Water | 672 |
| Fe | 2 |
| B-factors (Å$^2$) | |
| Protein | 30.12 |
| Water | 26.70 |
| Fe | 17.79 |
| R.m.s. deviations | |
| Bond lengths (Å) | 0.003 |
| Bond angles (°) | 0.714 |
| Ramachandran | |
| Outliers (%) | 0.0 |
| Favored (%) | 97.5 |

$^a$ Values in parentheses are for the highest resolution shell.

$^b R_{p.i.m.} = \sum h \left( \frac{1}{n_h - 1} \right) \sum l | I_{hl} - \langle I_h \rangle | / \sum h \sum l \langle I_h \rangle$ $^c R = \Sigma ||F_o| - |F_c||/\Sigma |F_o|$, where $F_o$ and $F_c$ are the observed and calculated structure factor amplitudes, respectively. $R_{free}$ was calculated using 3.2% of the total reflections.

As discussed above, based on the crystal structures of two AA-metabolizing lipoxygenases [an 8R-LOX from *Plexaura homomalla* (7, 10) and a 15-LOX from rabbit reticulocyte (11, 12)], each with ~40% sequence identity to 5-LOX), we identified a 5-LOX specific lysine-rich region near the C-terminus of the enzyme that might confer instability. In the 8R- and 15-LOX structures, a turn centered on amino acid 655 (5-LOX numbering) leads from the C-terminal helix to the carboxyl terminal segment, allowing the terminal carboxylate to penetrate the LOX body and bind the catalytic iron (FIGS. 6A, 6B). In most LOXs, amino acid 655 is a highly conserved Leu, with its side chain pointing toward an invariant Arg (651) as shown in FIG. 5. A striking 5-LOX specific feature is Lys in place of Leu at this position as part of a di- or tri-Lys peptide (FIG. 5).

FIG. 6A is a schematic representation of the superposition of the C-terminal regions of the structures of 15-lipoxygenase, 8R-lipooxygenase, and Stable-5-lipooxygenase. The C-terminal segment that leads to the catalytic Fe emanates from the helix which terminates at amino acid 655 (native human 5-LOX numbering). Highly conserved amino acids (Leu, Phe/Tyr) and an invariant salt link (473Asp-651Arg) are depicted in stick rendering.

FIG. 6B is a schematic representation of the turn at the end of the terminal helix. The 5-LOX specific Lys (substituted in Stable-5-LOX with Leu) is modeled at position 655 as its most common rotamer (transparent sphere rendering). As positioned, it would interfere with the invariant salt-link and cation-π interactions. All figures were generated with PyMOL, a user-sponsored molecular visualization system on an open-source foundation (Schrödinger, L.L.C., Rockville, Md.).

While numerous salt links anchor the C-terminal helix to the body of the protein in the structures of the two homologues noted above, none of these salt links is conserved in the 5-LOX sequence. As a consequence of the lysine-rich sequence and the absence of helix-anchoring salt-links, the orientation of the terminal helix is less favorable and the C-terminal ligand to the active site Fe is likely to be tenuously restrained. Conservative mutations in the carboxy terminal helix have been noted to reduce enzyme expression levels and activity (13). Thus Stable-5-LOX was made to replace 5-LOX $KKK_{653-655}$ with the corresponding sequence from 8R-LOX (ENL) in an effort to stabilize the enzyme for crystallographic studies.

Stable-5S-LOX was prepared in the context of a soluble 5-LOX (Sol-5-LOX) which lacks putative membrane insertion amino acids (Δ40-44GS, W13E, F14H, W75G, L76S) as well as a pair of Cysteines (C240A, C561A) predicted to be proximal in the 5-LOX structure. The amino acids to be changed and the subsequent changes are all indicated in FIGS. 1-4 as bolded and underlined. Substitution of the membrane insertion loops was based on a similar approach with the *Plexaura homomalla* enzyme, which shares both these amino acids and $Ca^{2+}$-binding residues with 5-LOX in the amino terminal membrane-binding domain (14). As shown in FIG. 6D, substitution of KKK with ENL in this context led to a ~3° C. increase in the melting temperature of the enzyme (FIG. 6C). FIG. 6C shows the thermal denaturation graphs of Stable-5-LOX and the parent enzyme Sol-5-LOX. Fluorescence (F) was monitored as a function of temperature. $T_m$ (with s.d.) was measured to be 56.6 (±0.4) and 59.7(±0.2)° C. for Sol-5-LOX and Stable-5-LOX, respectively.

Moreover, Stable-5S-LOX has a longer half-life at 37° C. (~16 hrs vs. ~7 hrs. FIG. 7). FIG. 7 shows the enzyme half-life for both Sol-5-LOX and Stable-5-LOX by monitoring enzyme activity (($\Delta A_{238}$) over the course of 24 hrs at 37° C.

Figure 9:
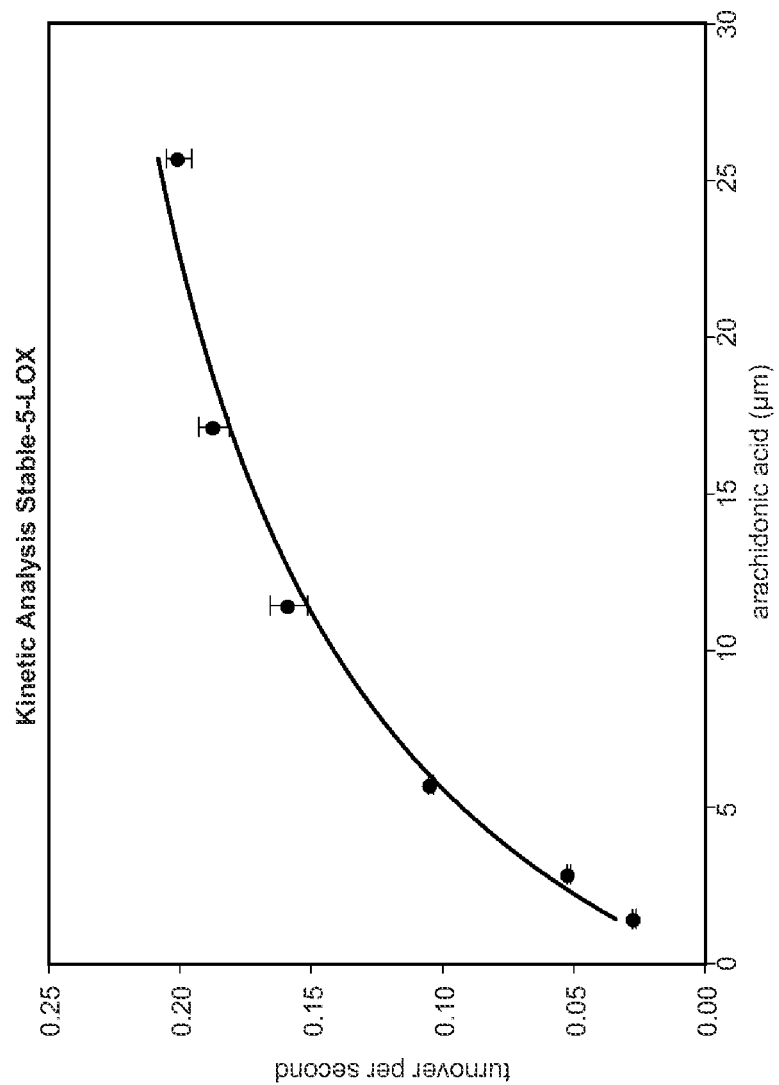
FIG. 9 shows the kinetic analysis of Stable-5-LOX activity as a function of substrate (arachidonic acid) concentration. A non-linear regression analysis yielded the hyperbolic curve, and the $K_M$ of Stable-5-LOX for arachidonic acid was found to be 11.1±2.1 μM.

Furthermore, Stable-5-LOX produces both the intermediate 5S-HPETE and the product leukotriene $A_4$ (FIG. 6D), as does its progenitor protein Sol-5-LOX (FIG. 8). FIG. 6D is an HPLC chromatogram of the products of Stable-5-LOX showing the production of both 5-HETE (5-HPETE reduced by the addition of triphenylphosphine, TPP) and Leukotriene $A_4$ hydrolysis products (5,12 diols). FIG. 8 is an HPLC chromatogram of the products of Sol-5-LOX showing the production of both 5-HETE (5-HPETE reduced by the addition of triphenylphosphine, TPP) and Leukotriene $A_4$ hydrolysis products (5,12 diols). In addition, we measured a $K_m$ for AA of ~11 µM (FIG. 9), equivalent to that of the wild-type enzyme (15). FIG. 9 shows the kinetic analysis of Stable-5-LOX activity as a function of substrate (arachidonic acid) concentration. A non-linear regression analysis yielded the hyperbolic curve, and the Kr of Stable-5S-LOX for arachidonic acid was found to be 11.1±2.1 µM.

Figure 10A:
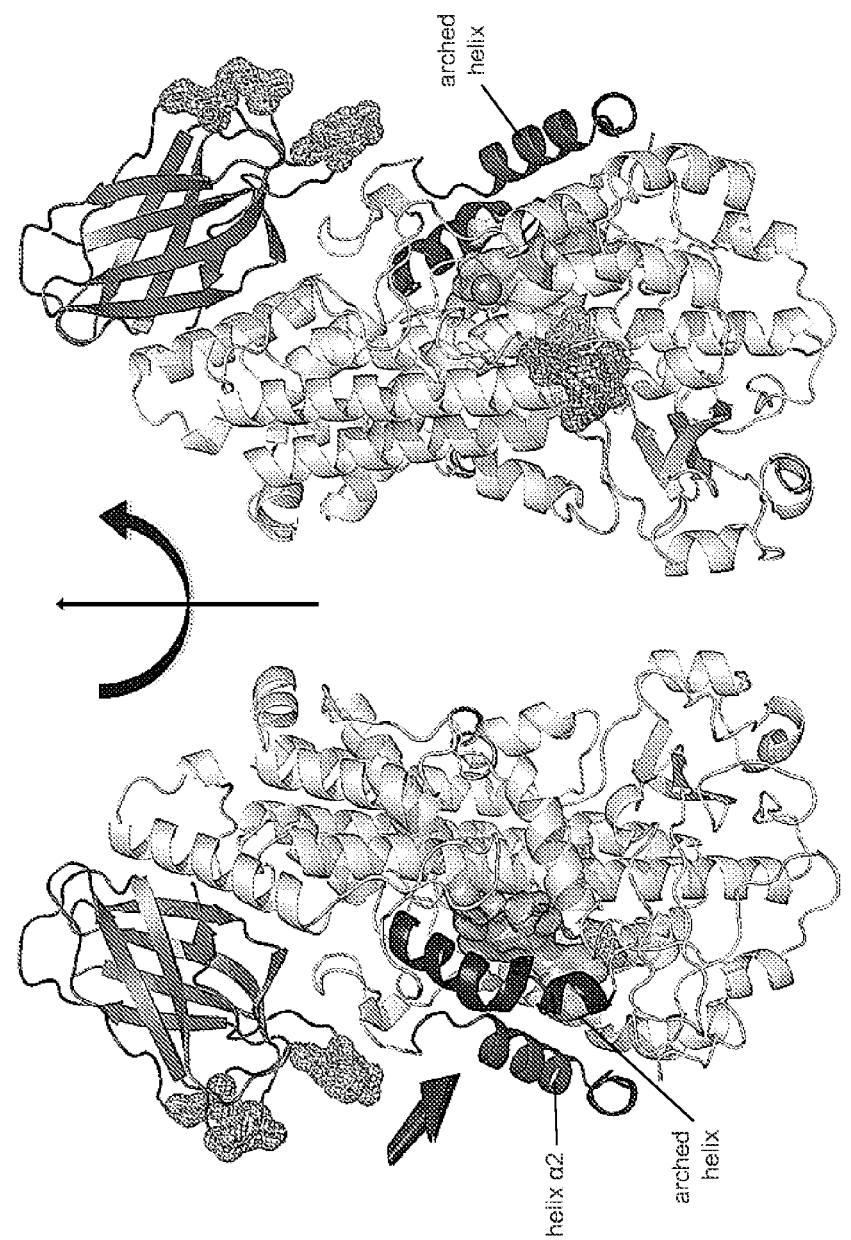
FIG. 10A is a schematic representation of 5-LOX in two views, differing by a 180° rotation about the vertical line. The amino terminal C2-like domain is seen as the beta-sheet ribbons at the top, and the catalytic domain is a shaded area near the Fe in the center. The distinctive arched helix is labeled "arched helix" and the helix α2 is labeled "helix α2"). The positions of the mutated amino acids are indicated in mesh rendering.
Figure 10B:
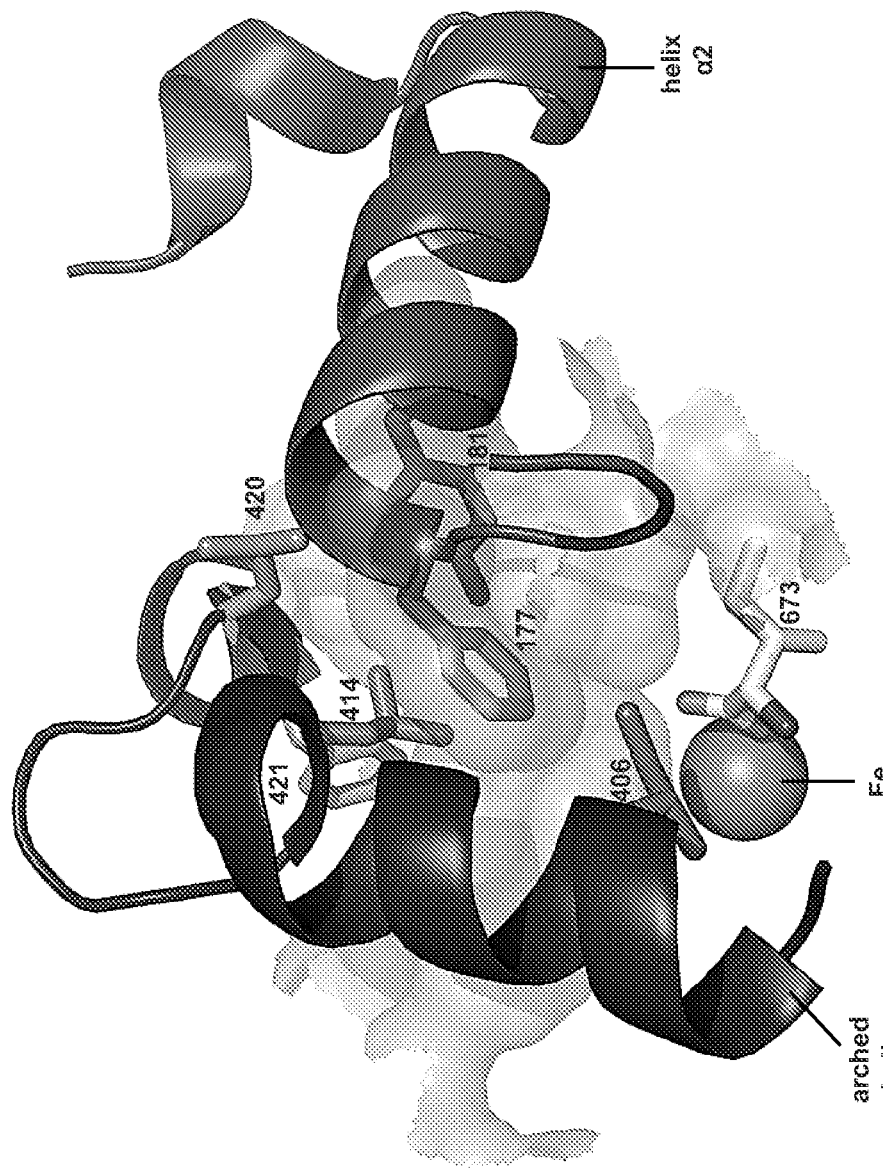
FIG. 10B is a schematic representation of the relationship of the arched helix and helix α2 to the active site as viewed from the perspective indicated by the arrow in FIG. 10A. Shown in stick rendering are amino acids 406, 414, 420, 421 of the arched helix and F177 and Y181 from helix α2 (with transparent surface rendering). The latter two bulky amino acids obstruct access to the active-site cavity. The proximity of the C-terminal Ile (I673) to the corked portal is apparent.
Figure 11:
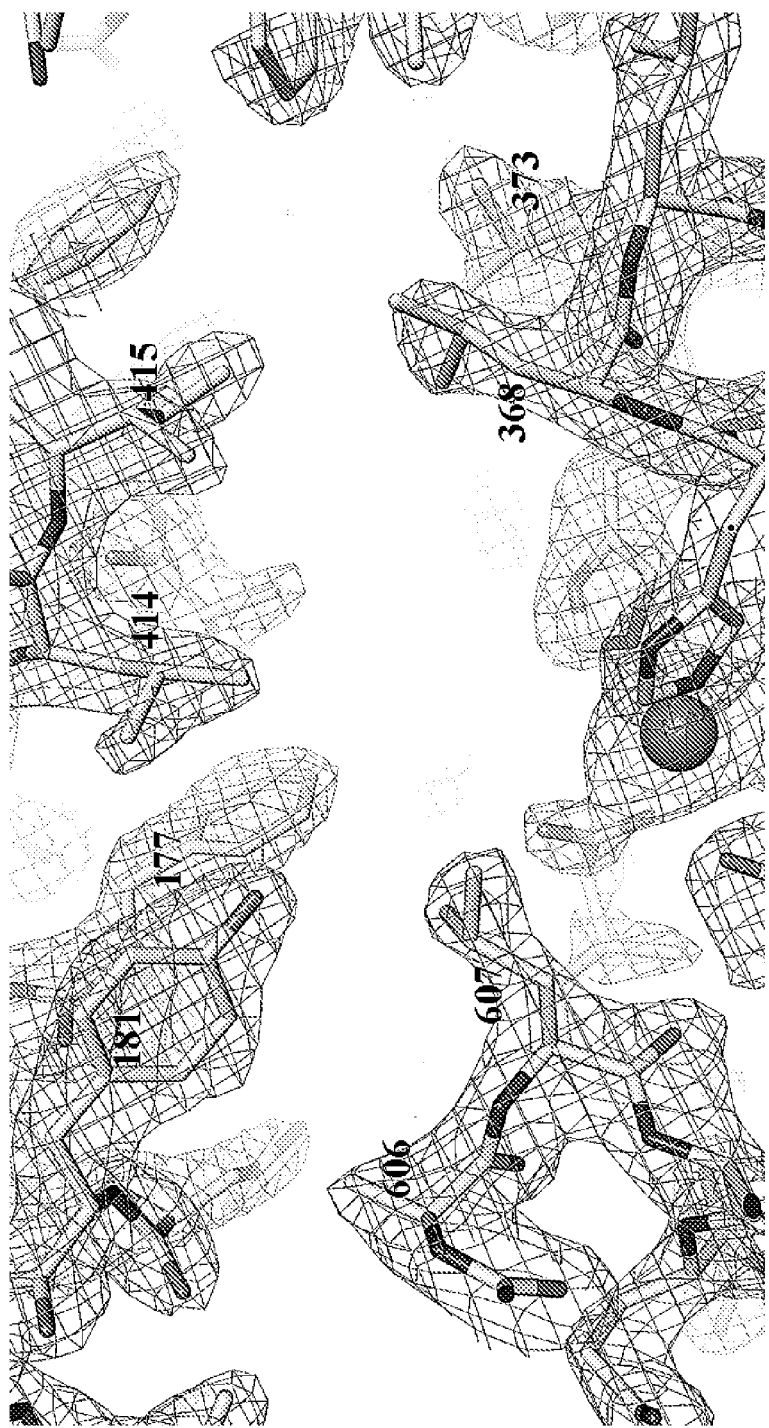
FIG. 11 is a schematic representation of electron density (2|Fo|−|Fc| density) in the active site cavity of Stable-5-LOX contoured at 1.5σ.

The above observations are consistent with the proposal that the KKK sequence is destabilizing, and that its substitution does not impact catalytic fidelity. The structure of Stable-5-LOX was determined to 2.4 Å resolution (FIG. 10A; FIG. 10B, FIG. 11; Table 1). FIG. 10A is a schematic representation of 5-LOX in two views, differing by a 180° rotation about the vertical line. The amino terminal C2-like domain is seen as the beta-sheet ribbons at the top, and the catalytic domain is a shaded area near the Fe in the center. The distinctive arched helix is labeled "arched helix" and the helix α2 is labeled "helix α2). The positions of the mutated amino acids are indicated in mesh rendering. FIG. 10B is a schematic representation of the relationship of the arched helix and helix α2 to the active site as viewed from the perspective indicated by the arrow in FIG. 10A. Shown in stick rendering are amino acids 406, 414, 420, 421 of the arched helix and F177 and Y181 from helix α2 (with transparent surface rendering). The latter two bulky amino acids obstruct access to the cavity. The proximity of the C-terminal Ile (I673) to the corked portal is apparent. FIG. 11 is a schematic representation of electron density (2|Fo|–|Fc| density) in the active site cavity of Stable-5-LOX contoured at 1.5σ.

Further schematic representations were made to show 5-LOX and its unique structure as compared to other LOXs. FIG. 12A is a schematic representation showing the positioning of helix α2 is unique in 5-LOX as compared to comparable sections of 15-LOX and 8R-LOX. Conserved aromatic amino acids (F169, W201) that flank the region are in stick rendering. F177 and Y181 that make up the "cork" that helps define the active site are in stick. The catalytic iron is shown as a sphere near the center. FIG. 12B is a schematic representation of a full overlay of the three structures for 5-LOX, 15-LOX and 8R-LOX in which it is apparent that, with the exception of the helix α2, the secondary structural elements in the enzymes are conserved. The box indicates the region amplified in FIG. 12A. FIG. 13A shows the active site cavity of 15-LOX (2P0M) calculated with CastP (30) as the lighter grey area. Invariant Leu and Ile side chains (362, 367, 400, 408 and 597) are in stick rendering. The 5-LOX "FY cork", F177 and Y181, a darker grey, is superposed on the 15-LOX cavity and plugs the entrance. FIG. 13B shows the active site cavity of Stable-5-LOX calculated with CastP (30) in an equivalent orientation of the active site cavity to that seen for 15-LOX in FIG. 13A. Invariant Leu and Ile side chains (368, 373, 406, 414, and 607) are in stick rendering. Note the similarity of the positions of these amino acids to their counterparts in 15-LOX in FIG. 13A. Iron coordination sphere amino acids (367, 372, 550, 554, and 673) are also seen in stick rendering, and the iron an orange sphere. FIG. 13C shows the active site cavity of Stable-5-LOX calculated with CastP (30), with the 5-LOX amino acids (147, 177, 181, 364, 407, 420, 421, 432, 599, 600, 603, and 606) that contribute to the active site cavity in stick rendering. Entry into this cavity requires a conformational change of the enzyme.

The canonical LOX framework contains two distinct domains: the amino terminal "C2-like" domain (~120 amino acids), which in 5-LOX confers $Ca^{2+}$-dependent membrane binding (16-19), and the larger catalytic domain. The latter is primarily α-helical and harbors the non-heme catalytic iron. The iron is coordinated by three conserved histidines (His-367, 372, 550) as well as the main-chain carboxylate of the C-terminus (I673) as shown in FIG. 13B. Another structurally distinct conserved feature in this domain, previously described in detail by Minor et al (20) for soybean LOX L-1, is an arched helix that shields access to the catalytic iron. At the vertex of the Stable-5-LOX arched helix is Leu-414 (FIG. 10B), an invariant amino acid that in other lipoxygenases has been proposed to control access of $O_2$ to the substrate (21, 22) or position the substrate pentadiene for attack (7). Additional amino acids from the arched helix that help define the catalytic site are Leu-420 and Phe-421.

The crystal structure of Stable-5-LOX reveals a striking variation on the classic lipoxygenase fold in helix α2 which defines one edge of the active site. In the structures of 8R- and 15-LOX helix α2 is 6-7 turns, while in Stable-5-LOX it is a short 3-turn helix flanked by extended loops. The shortened helix is positioned at ~45° to its counterparts in the 8R- and 15S-enzymes (FIGS. 12A and 12B). The unique orientation of helix α2 in Stable-5-LOX greatly limits access to the catalytic iron and yields a distinctive active site cavity. Specifically, the side chains of F177 and Y181 are positioned inward and close off an access channel to the catalytic iron that is observed in both the 8R- and 15-LOX structures (FIG. 10B, FIG. 13A). The remainder of the secondary structural elements, and their relative orientations, are maintained (FIG. 12B). In addition, the structural context of the Lys-rich peptide also appears conserved as the C-terminal helices superimpose (FIG. 6A). However, it is apparent that a Lys at position 655 would interfere with invariant salt link and cation-π interactions (FIG. 6B).

In Stable-5-LOX the active site is an elongated cavity, with no clear access to bulk solvent, lined with both invariant and 5-LOX specific amino acids. Leu-368, 373, 414, 607 and Ile-406 are conserved in all AA-metabolizing lipoxygenases (7) and form a structurally similar constellation of branched hydrophobic side chains that envelop the region where the pentadiene must be positioned for catalysis (FIG. 13A and FIG. 13B). Y181, A603, A606, H600 and T364 are specific to 5-LOX sequences and the small side chains of A603 and A606 appear to be required for the conformation of Y181 which, along with F177, "corks" the cavity at one end. Y181 is in van der Waals contact with A603, and the small side chains of both 603 and 606 allow both bulky aromatics (F177, Y181) to point into the cavity where they can be shielded from solvent (FIG. 4C). An additional 5-LOX specific amino acid, W599, appears to buttress the FY cork from one side. Amino acids Asn-407 and His-432 also help define the active site.

The closed cavity (volume=663 Å$^3$) raises the question of how substrate gains access to the catalytic iron. Two possibilities can be envisioned: (1) Removal of the FY cork at one end of the cavity and/or movement of W599 that secures it; or (2) A rotamer shift of W147 at the opposite end. A rotamer shift in W147 would require only rotation of the side chain, while the former may require both side chain and main chain movements in two amino acids. This observation suggests that AA may enter 5-LOX from the opposite direction as it does in the 15S- or 8R-enzymes, which lack the FY cork. This site of entry fits well with what is known about the catalytic mechanism: H abstraction and peroxidation occur on opposite sides of the pentadiene (23). The S-stereochemistry of the 5-LOX product is consistent with an "inverse" orientation of AA relative to that for the 15S- and 8R-enzymes (24, 25). An opening at the W147 end would allow the AA to enter methyl end first and position the substrate for the production of the S isomer of 5-HPETE. While the above model is attractive, the structure does not rule out the alternative: that the AA enters the same portal it does in 8R- and 15S-enzymes. Carboxylate-first entry in this latter mode achieves the same binding orientation and reaction specificity.

The 2.4 Å structure of Stable-5-LOX reveals an active site which, despite a conserved constellation of five invariant amino acids, is clearly distinct from the active sites of the arachidonic acid metabolizing lipoxygenases for which structures are available. The structure provides a context for the development of 5-LOX specific inhibitors and together with the crystal structures of FLAP (26) and the downstream enzyme Leukotriene C$_4$ Synthase (27, 28), a molecular model for early events in leukotriene biosynthesis.

REFERENCES

1. J. F. Evans, A. D. Ferguson, R. T. Mosley, J. H. Hutchinson, *Trends Pharmacol Sci* 29, 72 (February, 2008).
2. R. A. Dixon et al., *Nature* 343, 282 (Jan. 18, 1990).
3. O. Radmark, B. Samuelsson, *J Lipid Res* 50 Suppl, S40 (April, 2009).
4. T. Shimizu, O. Radmark, B. Samuelsson, *Proc Natl Acad Sci USA* 81, 689 (February, 1984).
5. R. C. Murphy, M. A. Gijon, *Biochem J* 405, 379 (Aug. 1, 2007).
6. M. D. Percival, D. Denis, D. Riendeau, M. J. Gresser, *Eur J Biochem* 210, 109 (Nov. 15, 1992).
7. D. B. Neau et al., *Biochemistry* 48, 7906 (Aug. 25, 2009).
8. Y. Y. Zhang, M. Hamberg, O. Radmark, B. Samuelsson, *Anal Biochem* 220, 28 (July, 1994).
9. J. M. Canadillas et al., *Proc Natl Acad Sci USA* 103, 2109 (Feb. 14, 2006).
10. M. L. Oldham, A. R. Brash, M. E. Newcomer, *J Biol Chem* 280, 39545 (Nov. 25, 2005).
11. S. A. Gillmor, A. Villasenor, R. Fletterick, E. Sigal, M. F. Browner, *Nat Struct Biol* 4, 1003 (1997).
12. J. Choi, J. K. Chon, S. Kim, W. Shin, *Proteins* 70, 1023 (Feb. 15, 2008).
13. H. Kuhn, M. Anton, C. Gerth, A. Habenicht, *Arterioscler Thromb Vase Biol* 23, 1072 (Jun. 1, 2003).
14. D. B. Neau, N. C. Gilbert, S. G. Bartlett, A. Dassey, M. E. Newcomer, *Acta Cystallographica Section F* 63, 972 (2007).
15. D. Aharony, R. L. Stein, *J Biol Chem* 261, 11512 (Sep. 5, 1986).
16. X. S. Chen, Y. Y. Zhang, C. D. Funk, *J Biol Chem* 273, 31237 (Nov. 20, 1998).
17. X. S. Chen, C. D. Funk, *J Biol Chem* 276, 811 (Jan. 5, 2001).
18. T. Hammarberg, K. V. Reddy, B. Persson, O. Radmark, *Adv Exp Med Biol* 507, 117 (2002).
19. S. Kulkarni, S. Das, C. D. Funk, D. Murray, W. Cho, *J Biol Chem* 277, 13167 (Apr. 12, 2002).
20. W. Minor et al., *Biochemistry* 35, 10687 (1996).
21. M. J. Knapp, J. P. Klinman, *Biochemistry* 42, 11466 (Oct. 7, 2003).
22. M. J. Knapp, F. P. Seebeck, J. P. Klinman, *J Am Chem Soc* 123, 2931 (Mar. 28, 2001).
23. C. Schneider, D. A. Pratt, N. A. Porter, A. R. Brash, *Chem Biol* 14, 473 (May, 2007).
24. M. Walther, I. Ivanov, G. Myagkova, H. Kuhn, *Chem Biol* 8, 779 (August, 2001).
25. G. Coffa, A. R. Brash, *Proc Natl Acad Sci USA*, (10 20, 2004).
26. A. D. Ferguson et al., *Science* 317, 510 (Jul. 27, 2007).
27. H. Ago et al., *Nature* 448, 609 (Aug. 2, 2007).
28. D. Martinez Molina et al., *Nature* 448, 613 (Aug. 2, 2007).
29. J. Dundas et al., *Nucleic Acids Res* 34, W116 (Jul. 1, 2006).
30. F. W. Studier, *Protein Expr Purif* 41, 207 (May, 2005).
31. U. B. Ericsson, B. M. Hallberg, G. T. Detitta, N. Dekker, P. Nordlund, *Anal Biochem* 357, 289 (Oct. 15, 2006).
32. Collaborative Computational Project, *Acta Crystallogr D Biol Crystallogr* 50, 760 (1994).
33. P. Emsley, K. Cowtan, *Acta Crystallogr D Biol Crystallogr* 60, 2126 (December, 2004).
34. P. H. Zwart et al., *Methods Mol Biol* 426, 419 (2008).
35. Brash, A. R., *J Biol Chem,* 274 (34): p. 23679-82 (1999).
36. Kuhn, H. and B. J. Thiele, *FEBS Lett,* 449 (1): p. 7-11 (1999).
37. Hughes, M. A. and A. R. *Biochim Biophys Acta,* 1081 (3): p. 347-54 (1991).

The complete disclosures of all references cited in this specification are hereby incorporated by reference. Also incorporated by reference are the complete disclosures of the following: (1) N. C. Gilbert et al., "The Structure of Human 5-Lipoxygenase," Science, vol. 331, pp. 217-219 (2011), including the Supporting Online Material for this article; and (2) N. C. Gilbert et al., "The Crystal Structure of Human 5-Lipoxygenase", an abstract and poster for the Keystone Conference, Bioactive Lipids: Biochemistry and Diseases, in Kyoto, Japan, Jun. 6, 2010.

What is claimed is:

1. An isolated 5-Lipoxygenase polypeptide comprising an amino acid sequence, numbered from the N-terminus, as set forth in SEQ ID NO: 1 with one or more of the following modifications selected from the group consisting of:
   (a) a replacement of amino acids Tryptophan and Phenylalanine at residues 13-14 with Glutamic acid and Histidine, respectively;
   (b) a replacement of amino acids Proline, Phenylalanine, Tyrosine, Asparagine and Aspartic Acid at residues 40-44 with Glycine-Serine;
   (c) a replacement of amino acids Tryptophan and Leucine at residues 75-76 with Glycine and Serine, respectively;
   (d) a replacement of amino acid Cysteine at residue 240 with Alanine;
   (e) a replacement of amino acid Cysteine at residue 561 with Alanine; and
   (f) a replacement of amino acids Lysine, Lysine and Lysine at residues 653-655 with Glutamic acid, Asparagine, and a non-positively charged amino acid, respectively.

2. The isolated 5-Lipoxygenase polypeptide of claim 1, wherein the polypeptide further comprises an amino terminus sequence that includes a multiple histidine sequence.

3. The isolated 5-Lipoxygenase polypeptide of claim 1, wherein the polypeptide further comprises a replacement of amino acid Serine at residue 663 with Aspartic Acid.

4. An isolated, soluble 5-Lipoxygenase polypeptide comprising an amino acid sequence selected from the group consisting of SEQ ID NO: 2, SEQ ID NO: 3 and SEQ ID NO: 4.

5. An isolated, stable 5-Lipoxygenase (5-LOX) polypeptide comprising an amino acid sequence, numbered from the N-terminus, as set forth in SEQ ID NO: 1 with a replacement of amino acids Lysine, Lysine and Lysine at residues 653-655 with Glutamic acid, Asparagine, and a non-positively charged amino acid, respectively.

6. An isolated, stable 5-Lipoxygenase (5-LOX) polypeptide comprising an amino acid sequence, numbered from the N-terminus, as set forth in SEQ ID NO: 1 with a replacement of amino acid Lysine at residue 655 with an amino acid having a non-positive charge.

7. An isolated, soluble and stable 5-Lipoxygenase polypeptide comprising an amino acid sequence, numbered from the N-terminus, as set forth in SEQ ID NO: 1 with the following modifications:
   (a) a replacement of amino acids 13-14 with Glutamic acid and Histidine, respectively;
   (b) a replacement of amino acids 40-44 with Glycine-Serine;
   (c) a replacement of amino acids 75-76 with Glycine and Serine, respectively;
   (d) a replacement of amino acid 240 with Alanine;
   (e) a replacement of amino acid 561 with Alanine; and
   (f) a replacement of amino acids 653-655 with Glutamic acid, Asparagine, and Leucine, respectively.

8. A crystalline 5-lipoxygenase comprising the amino acid sequence as set forth in SEQ ID NO: 3 or SEQ ID NO: 4, wherein said crystalline 5-lipoxygenase has space group $P2_1$, and unit cell dimensions a=55.17 Å±0.003 Å, b=202.89 Å±0.003 Å, c=76.80 Å±0.003 Å, and b=109.56°±0.714°.

9. An isolated nucleic acid molecule encoding the 5-Lipoxygenase polypeptide according to claim 1.

10. An isolated nucleic acid molecule encoding the 5-Lipoxygenase polypeptide according to claim 2.

11. An isolated nucleic acid molecule encoding the 5-Lipoxygenase polypeptide according to claim 3.

12. An isolated nucleic acid molecule encoding the 5-Lipoxygenase polypeptide according to claim 4.

13. An isolated nucleic acid molecule encoding the 5-Lipoxygenase polypeptide according to claim 5.

14. An isolated nucleic acid molecule encoding the 5-Lipoxygenase polypeptide according to claim 6.

15. An isolated nucleic acid molecule encoding the 5-Lipoxygenase polypeptide according to claim 7.

* * * * *